United States Patent
Chuaqui et al.

(10) Patent No.: US 7,226,731 B1
(45) Date of Patent: Jun. 5, 2007

(54) PB 39, A GENE DYSREGULATED IN PROSTATE CANCER, AND USES THEREOF

(75) Inventors: Rodrigo F. Chuaqui, Bethesda, MD (US); Kristina A. Cole, Swarthmore, PA (US); Lance A. Liotta, Bethesda, MD (US); Michael R. Emmert-Buck, Easton, MD (US)

(73) Assignee: The United States of America, as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/743,825

(22) PCT Filed: Jul. 23, 1999

(86) PCT No.: PCT/US99/16831

§ 371 (c)(1),
(2), (4) Date: Jan. 15, 2002

(87) PCT Pub. No.: WO00/05376

PCT Pub. Date: Feb. 3, 2000

Related U.S. Application Data

(60) Provisional application No. 60/094,137, filed on Jul. 24, 1998.

(51) Int. Cl.
*C12Q 1/68* (2006.01)

(52) U.S. Cl. .................. 435/6; 435/91.1; 435/91.2; 435/94; 538/23.1; 538/23.5; 538/24.3; 538/24.33

(58) Field of Classification Search ............ 536/23.1, 536/23.5, 24.3, 24.33; 435/64.1, 325, 252.3, 435/320.1, 6, 91.1, 91.2, 94
See application file for complete search history.

(56) References Cited

U.S. PATENT DOCUMENTS

| | | | |
|---|---|---|---|
| 5,330,892 A | 7/1994 | Vogelstein et al. ........... 435/6 |
| 5,380,645 A | 1/1995 | Vogelstein ................... 435/6 |
| 5,501,983 A | 3/1996 | Lilja et al. .................. 436/518 |
| 5,506,106 A | 4/1996 | Croce et al. .................. 435/6 |
| 5,543,296 A | 8/1996 | Sobol et al. .................. 435/6 |
| 5,552,277 A | 9/1996 | Nelson et al. ................. 435/6 |
| 5,567,586 A | 10/1996 | Croce .......................... 435/6 |
| 5,569,753 A | 10/1996 | Wigler et al. .............. 536/24.3 |
| 5,571,710 A | 11/1996 | Barnett et al. ........... 435/240.1 |
| 5,582,972 A | 12/1996 | Lima et al. ................... 435/6 |
| 5,591,582 A | 1/1997 | Bos et al. ..................... 435/6 |
| 5,605,799 A | 2/1997 | White et al. .................. 435/6 |
| 5,614,372 A | 3/1997 | Lilja et al. .................... 435/6 |
| 5,622,829 A | 4/1997 | King et al. ................... 435/6 |
| 5,648,212 A | 7/1997 | Albertson et al. ........... 435/6 |
| 5,650,500 A | 7/1997 | Raz et al. .................. 536/23.1 |
| 5,658,730 A | 8/1997 | McGill et al. ................ 435/6 |
| 5,674,682 A | 10/1997 | Croce et al. .................. 435/6 |
| 5,763,202 A | 6/1998 | Horoszewicz ............. 435/7.23 |
| 5,912,143 A * | 6/1999 | Bandman et al. ......... 435/69.1 |

FOREIGN PATENT DOCUMENTS

| | | |
|---|---|---|
| WO | WO 098/10098 | 3/1998 |
| WO | WO 98/21328 | 5/1998 |

OTHER PUBLICATIONS

Bowie et al (Science, 1990, 257: 1306-1310).*
Burgess et al, (Journal of Cell Biology, 1990, 11: 2129-2138).*
Lazar et al. Molecular and Cell Biology, 1988, 8: 1247-1252.*
Tao. et al. The Journal of Immunology, 1989, 143(8): 2595-2601.*
Gillies et al. Human Antibodies and Hybridomas, 1990, 1(1): 47-54.*
Sambrook et al, eds, 1989, 2nd ed, Molecular Cloning, a laboratory manual, Cold Spring Harbor Laboratory Press, Cold Spring Harbor, p. 11.52.*

(Continued)

*Primary Examiner*—Jeffrey Siew
*Assistant Examiner*—Minh-Tam Davis
(74) *Attorney, Agent, or Firm*—Venable LLP; Thomas G. Wiseman; Nancy J. Axelrod

(57) ABSTRACT

A novel gene, PB39, that is up-regulated, or over-expressed, in prostate cancer has been identified. The gene has been identified by means of its cDNA obtained by reverse transcription of the corresponding mRNA. Microdissection of prostate glands that had been surgically removed from prostate cancer patients revealed a novel up-regulated transcript in an aggressive prostate carcinoma. Differential analysis for the presence of this gene was carried out from the same glands by comparing transcription in microdissected normal prostatic epithelium versus that in microdissected invasive tumor. The transcript was over-expressed in 5 of 10 prostate carcinomas examined. A variant transcript was over-expressed in 4 of 4 prostate carcinomas, and was found in 1 of 4 normal samples. The invention provides a purified and isolated nucleic acid that includes the sequence of PB39 or its complement, the sequence of a variant of PB39 or its complement, and a primer or probe, that includes a sequence that is a fragment of these sequences. Additionally, the polypeptide encoded by these genes, an antibody to the polypeptide, and methods of detection of PB39 or its gene product are provided.

13 Claims, 7 Drawing Sheets

OTHER PUBLICATIONS

Kibel, AS et al, 2000, J urol, 164(1): 192-6.*
Zhau, HE, 1994, J Cell Biochem, Suppl 19: 208-216.*
Cheung S T et al, 2002, Cancer Research, 62(16): 4711-21.*
Ren, C et al, 1998, Cancer Res, 58(6): 1285-90.*
Gingrich, JR et al, 1996, Cancer res, 56(18):4096-4102.*
Boehringer Mannheim Biochemicals, 1994 Catalog, p. 93.*
MPSRCH sequence search report, 2004, us-09-743-825-1.rng, pp. 4-6.*
Genbank Sequence Database, Accession No: G22380, and MPSRCH search report, 2004, us-09-743-825-7.rge, p. 1-2, and us-09-743-825-10.rge, p. 1-2.*
JP08154685-A, and MPSRCH search report, 2006, us-09-743825-7.rng, pp. 7-8.*
US 6,509,163-B1, and MPSRCH search report, 2006, us-09-743825-8rng, p. 4.*
US 6,849,399-B1, and MPSRCH search report, 2006, us-09-743825-10.rng, pp. 4.*
Phyllis A. Wingo et al., "*Cancer Statistics, 1995*," A Cancer Journal for Clinicians, vol. 45, No. 1, Jan./Feb. 1995, pp. 8-30.
Piotr Chomcsnynski et al., "*Single-Step Method for RNA Isolation by Acid Guanidinium Thiocyanate-Phenol-Chloroform Extraction*," Analytical Biochemestry 162, pp. 156-159, 1987.
Michael R. Emmert-Buck et al., "*Increased Gelatinase A (MMP-2) and Cathepsin B Activity in Invasive Tumor Regions of Human Colon Cancer Samples*," American Journal of Pathology, vol. 145, No. 6, pp. 1285-1290, Dec. 1994.
Zhengping Zhuang et al., "*A Microdissection Technique for Archival DNA Analysis of Specific Cell Populations in Lesions <1 mm in Size*," American Journal of Pathology, vol. 146, No. 3, pp. 620-625, Mar. 1995.
Brad Stone et al., "*Targeted RNA Fingerprinting: The Cloning of Differentially-Expressed cDMA Fragments Enriched for Members of the Zinc Finger Gene Family*," Nucleic Acids Research, vol. 22, No. 13, pp. 2612-2618, 1994.
Rodrigo F. Chuaqui et al., "*Identification of a Novel Transcript Up-Regulated in a Clinically Aggressive Prostate Carcinoma*," Urology, vol. 50, No. 2, pp. 302-307, 1997.
Michael R. Emmert-Buck et al., "*Laser Capture Microdissection*," Science, vol. 274, Nov. 8, 1996.
David G. Bostwick et al., "*Molecular Biology of Prostatic Intraepithelial Neoplasia*," The Prostate, vol. 29, pp. 117-34, 1996.

Samuel C. Mok et al., "*Molecular Cloning of Differentially Expressed Genes in Human Epithelial Ovarian Cancer*," Gynecological Oncology, vol. 52, pp. 247-252, 1994.
Olivier Kocher et al., "*Identification of a Novel Gene, Selectively Up-Regulated in Hujman Carcinomas, Using the Differential Display Technique*," Clinical Cancer Research, vol. 1, pp. 1209-1215, Oct. 1995.
Mark A. Watson et al., "*Isolation of Differentially Expressed Sequence Tags from Human Breast Cancer*," Cancer Research, vol. 54, pp. 4598-4602, Sep. 1, 1994.
Peng Liang et al., "*Differential Display and Cloning of Messenger RNAs from Human Breast Cancer versus Mammary Epithelian Cells*," Cancer Research, vol. 52, pp. 6966-6968 (Dec. 15, 1992.
Cole et al., "cDNA Sequencing and Analysis of POV1 (PB39): a Novel Gene Up-regulated in Prostate Cancer", *Genomics*, vol. 51, No. 2, Jul. 1998, pp. 282-287, XP002120985, p. 282, col. 1; Figures 1 and 2.
Wingo P. et al., "Cancer Statistics, 1995," *Cancer Journal for Clinicians*, vol. 45: No. 1, pp. 8-30 (1995).
Epstein J. et al., "Prediction of Progression Following Radical Prostatectomy: a Multivariate Analysis of 721 Men with Long-Term Follow-up", *American Journal of Surgical Pathology*, vol. 20, No. 1, pp. 286-292 (1996).
Kozak M., "Structural Features in Eukaryotic mRNAs That Modulate the Initiation of Translation," *The Journal of Biological Chemistry*, vol. 266, No. 30, pp. 19867-19870 (1991).
Kawana et al., "Location of KAL1 on the Short Arm of Human Chromosome II and Frequency of Allelic Loss in Advanced Human Prostate Cancer," *The Prostate*, vol. 32, No. 3, pp. 205-213 (1997).
Pinkel, D. et al., "Fluorescence In Situ Hybridization with Human Chromosome-specific Libraries: Detection of the Trisomy 21 and Translocations of Chromosome 4," *Proceedings of the National Academy of Sciences of the United States of America*, vol. 85, No. 23, pp. 9138-9142 (1988).
Hirai, M. et al., "A Method of Simultaneous Detection of Fluorescent G-bands and In Situ Hybridization Signals," *Cytogenetics and Cell Genetics*, vol. 66, No. 3, pp. 149-151 (1994).
Dong, J.T. et al., KAI1, a Metastasis Suppressor Gene for Prostate Cancer on Human Chromosome 11p11.2, *Science*, vol. 268, pp. 884-886 (1995).

* cited by examiner

Figure 1
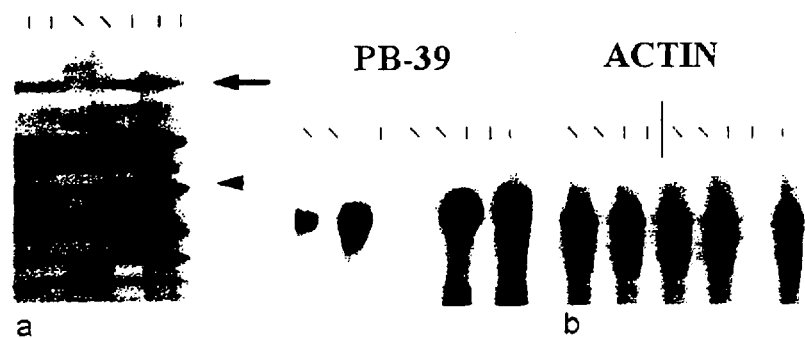
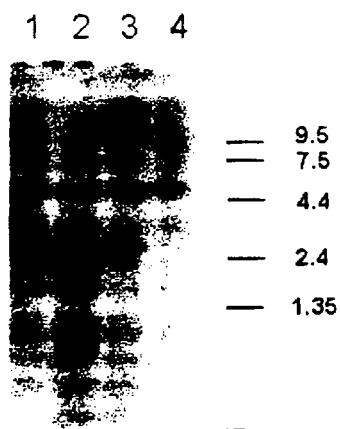
Figure 2

Fig. 4
Panel A

```
   1 ccggggctggagggggggcaagcgggttccgaggtgcaaagcctgg
     tgccccgagccctgcggagctcggggccagc
  77 atggcccccacgctgcaacaggcgtaccggaggcgctggtggatg
      M  A  P  T  L  Q  Q  A  Y  R  R  R  W  W  M   15
 122 gcctgcacggctgtgctggagaacctcttcttctctgctgtactc
      A  C  T  A  V  L  E  N  L  F  F  S  A  V  L   30
 167 ctgggctggggctccctgttgatcattctgaagaacgagggcttc
      L  G  W  G  S  L  L  I  I  L  K  N  E  G  F   45
 212 tattccagcacgtgcccagctgagagcagcaccaacaccacccag
      Y  S  S  T  C  P  A  E  S  S  T  N  T  T  Q   60
 257 gatgagcagcgcaggtggccaggctgtgaccagcaggacgagatg
      D  E  Q  R  R  W  P  G  C  D  Q  Q  D  E  M   75
 302 ctcaacctgggcttcaccattggttccttcgtgctcagcgccacc
      L  N  L  G  F  T  I  G  S  F  V  L  S  A  T   90
 347 accctgccactggggatcctcatggaccgctttggcccccgaccc
      T  L  P  L  G  I  L  M  D  R  F  G  P  R  P  105
 392 gtgcggctggttggcagtgcctgcttcactgcgtcctgcaccctc
      V  R  L  V  G  S  A  C  F  T  A  S  C  T  L  120
 437 atggccctggcctcccgggacgtggaagctctgtctccgttgata
      M  A  L  A  S  R  D  V  E  A  L  S  P  L  I  135
 482 ttcctggcgctgtccctgaatggctttggtggcatctgcctaacg
      F  L  A  L  S  L  N  G  F  G  G  I  C  L  T  150
 527 ttcacttcactcacgctgcccaacatgtttgggaacctgcgctcc
      F  T  S  L  T  L  P  N  M  F  G  N  L  R  S  165
 572 acgttaatggccctcatgattggctcttacgcctcttctgccatt
      T  L  M  A  L  M  I  G  S  Y  A  S  S  A  I  180
 617 acgttcccaggaatcaagctgatctacgatgccggtgtggccttc
      T  F  P  G  I  K  L  I  Y  D  A  G  V  A  F  195
 662 gtggtcatcatgttcacctggtctggcctggcctgccttatcttt
      V  V  I  M  F  T  W  S  G  L  A  C  L  I  F  210
 707 ctgaactgcaccctcaactggcccatcgaagcctttcctgctcct
      L  N  C  T  L  N  W  P  I  E  A  F  P  A  P  225
 752 gaggaagtcaattacacgaagaagatcaagctgagtgggctggcc
      E  E  V  N  Y  T  K  K  I  K  L  S  G  L  A  240
 797 ctggaccacaaggtgacaggtgacctcttctacacccatgtgacc
      L  D  H  K  V  T  G  D  L  F  Y  T  H  V  T  255
 842 accatgggccagaggctcagccagaaggcccccagcctggaggac
      T  M  G  Q  R  L  S  Q  K  A  P  S  L  E  D  270
 887 ggttcggatgccttcatgtcaccccaggatgttcggggcacctca
      G  S  D  A  F  M  S  P  Q  D  V  R  G  T  S  285
 932 gaaaaccttcctgagaggtctgtccccttacgcaagagcctctgc
      E  N  L  P  E  R  S  V  P  L  R  K  S  L  C  300
 977 tcccccactttcctgtggagcctcctcaccatgggcatgacccag
      S  P  T  F  L  W  S  L  L  T  M  G  M  T  Q  315
1022 ctgcggatcatcttctacatggctgctgtgaacaagatgctggag
      L  R  I  I  F  Y  M  A  A  V  N  K  M  L  E  330
1067 taccttgtgactggtggccaggagcatgagacaaatgaacagcaa
      Y  L  V  T  G  G  Q  E  H  E  T  N  E  Q  Q  345
1112 caaaaggctggcagagacagttgggttctactcctccgtcttcggg
      Q  K  V  A  E  T  V  G  F  Y  S  S  V  F  G  360
1157 gccatgcagctgttgtgccttctcacctgccccctcattggctac
      A  M  Q  L  L  C  L  L  T  C  P  L  I  G  Y  375
```

Figure 4 panel B

```
1202 atcatggactggcggatcaaggactgcgtggacgccccaactcag
      I  M  D  W  R  I  K  D  C  V  D  A  P  T  Q   390
1247 ggcactgtcctcggagatgccagggacggggttgctaccaaatcc
      G  T  V  L  G  D  A  R  D  G  V  A  T  K  S   405
1292 atcagaccacgctactgcaagatccaaaagctcaccaatgccatc
      I  R  P  R  Y  C  K  I  Q  K  L  T  N  A  I   420
1337 agtgccttcaccctgaccaacctgctgcttgtgggttttggcatc
      S  A  F  T  L  T  N  L  L  L  V  G  F  G  I   435
1382 acctgtctcatcaacaacttacacctccagtttgtgacctttgtc
      T  C  L  I  N  N  L  H  L  Q  F  V  T  F  V   450
1427 ctgcacaccattgttcgaggtttcttccactcagcctgtgggagt
      L  H  T  I  V  R  G  F  F  H  S  A  C  G  S   465
1472 ctctatgctgcagtgttcccatccaaccactttgggacgctgaca
      L  Y  A  A  V  F  P  S  N  H  F  G  T  L  T   480
1517 ggcctgcagtccctcatcagtgctgtgttcgccttgcttcagcag
      G  L  Q  S  L  I  S  A  V  F  A  L  L  Q  Q   495
1562 ccacttttcatggcgatggtgggacccctgaaaggagagcccttc
      P  L  F  M  A  M  V  G  P  L  K  G  E  P  F   510
1607 tgggtgaatctgggcctcctgctattctcactcctgggattcctg
           agagcgaggggttggtgtgggggggagcaggagccactctc
      W  V  N  L  G  L  L  L  F  S  L  L  G  F  L   525
        R  A  R  V  G  V  G  G  A  G  A  T  L       525
1652 ttgccttcctacctcttctattaccgtgcccggctccagcaggag
      ctgggggcaggggtagggccttgtatgtggtgccatccctcactc
      L  P  S  Y  L  F  Y  Y  R  A  R  L  Q  Q  E   540
      L  G  A  G  V  G  P  C  M  W  C  H  P  S  L   540
1697 tacgccgccaatgggatgggcccactgaaggtgcttagcggctcc
      atctcagccagaggcacctcagaggtctctaatctgcaggtttcc
      Y  A  A  N  G  M  G  P  L  K  V  L  S  G  S   555
      I  S  A  R  G  T  S  E  V  S  N  L  Q  V  S   555
1742 gaggtgaccgcatag       1756
      aagttgtctgccttttag   1759
      E  V  T  A  *  559
      K  L  S  A  F  *#560
```

```
acttctcagaccaagggacctggatgacaggcaatcaaggcctga
gcaaccaaaaggagtgccccatatggcttttctacctgtaacatg
cacatagagccatggccgtagatttataaataccaagagaagttc
tattttgtaaagactgcaaaaaggaggaaaaaaaaccttcaaaa
acgcccctaagtcaacgctccattgactgaagacagtccctatc
ctagaggggttgagcttttcttcctccttgggttggaggagaccag
ggtgcctcttatctccttctagcggtctgcctcctggtacctctt
gggggggatcggcaaacaggctaccccctgaggtcccatgtgccatg
agtgtgcacaacatgcaatgtgtctgtgtatgtgtgccatgaatg
tgagaaaaacacagccctcctttcagaaggaaaggggcctgaggg
ctgtgtcctgggttaggggttgggggtcggccccttccagggcca
ggaaggcaggttccctctctggtgctgctgcttgcaagtcttaga
ggaaataaaagggaagtgag aaaaaaaaa
``` there are approximately an additional 2300 nucleotides at
this site contributing to the 5 kb transcript's 3'UTR.

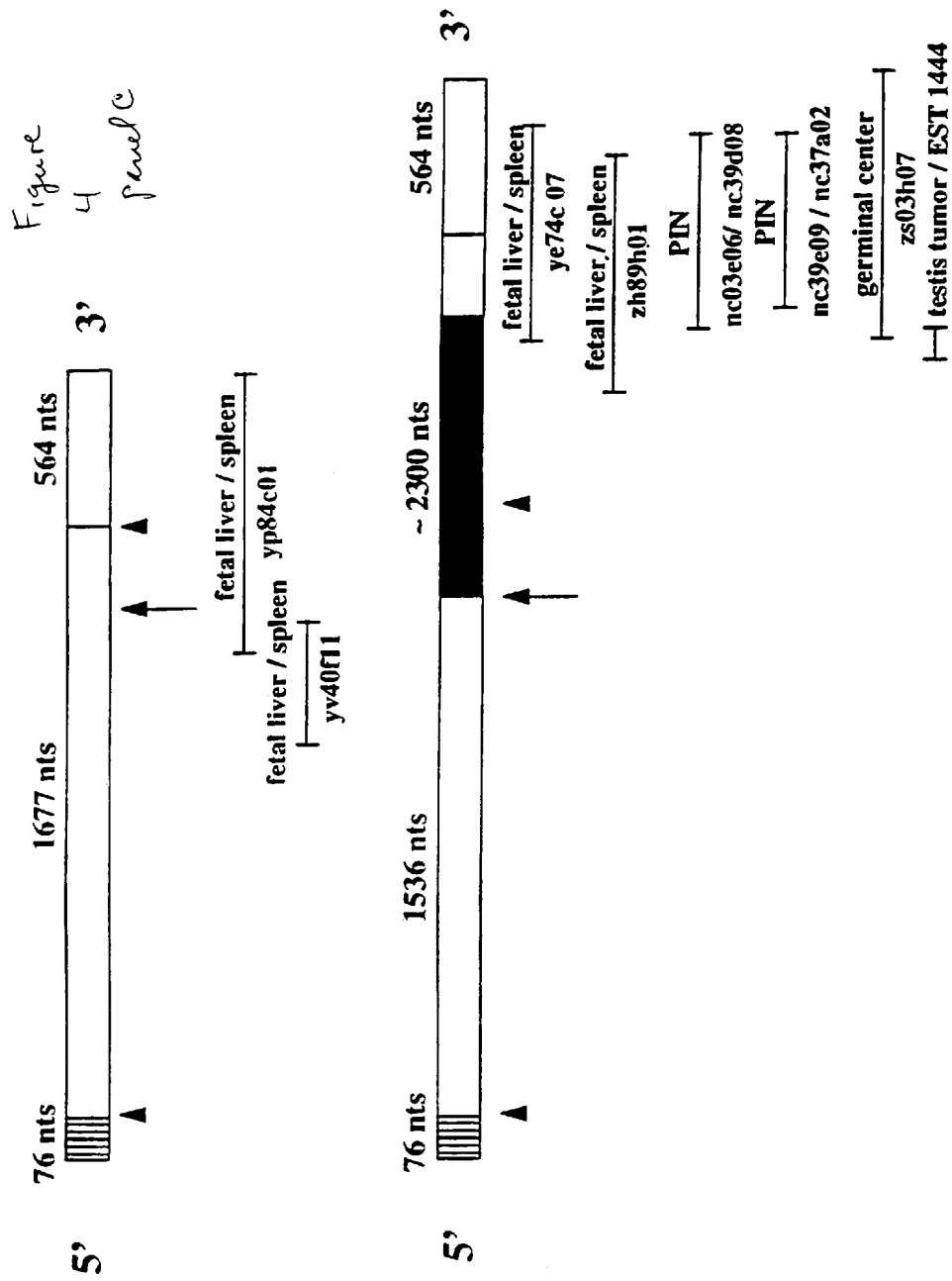

Figure 5
— 4.4 kb
— 2.4 kb
— 1.35 kb
Figure 6

PB 39, A GENE DYSREGULATED IN PROSTATE CANCER, AND USES THEREOF

RELATED APPLICATIONS

This application is a 371 national stage application of PCT/US99/16831, filed on Jul. 23, 1999, which claims benefit of Application Ser. No. 60/094,137, filed on Jul. 24, 1998, now abandoned.

FIELD OF THE INVENTION

This invention relates to a novel gene. PB39, and variants thereof, which is dys-regulated in prostate cancer. This invention also relates to polypeptides encoded by these genes, antibodies to the polypeptides, and to methods for detection of PB39, variants thereof, and/or its gene product. These methods can be used to assess the presence of precancerous or cancerous cells in the prostate gland.

BACKGROUND OF THE INVENTION

Prostate cancer is the most common malignancy in men and the second leading cause of cancer mortality in the United States (Wingo P. et al., Cancer statistics, Cancer J Clin 45: 8-30 (1995)). The disease can progress with markedly different clinical outcomes. An understanding of the difference between aggressive and nonaggressive tumors at the molecular level has been hindered by the diverse cell types present in the prostate gland and an inability to derive pure cell populations for genetic study.

The Gleason score is a reliable prognosticator for disease progression at both ends of the histologic spectrum ($\leq 4$ or $\geq 8$). Poor disease outcome in the more prevalent Gleason range (5 to 7) is best predicted by a positive surgical margin, capsular penetration, and seminal vesicle invasion (Epstein J. et al., Prediction of progression following radical prostatectomy: a multivariate analysis of 721 men with long-term follow-up, Am J Surg Pathol 20: 286-292 (1996)). However, these parameters can only be assessed after major surgery. Certain cases of prostate cancer respond to surgical and/or pharmaceutical intervention. Others metastasize rapidly, by mechanisms that remain poorly understood, to tissues such as bone.

Currently available diagnostic methods directed to the detection of prostate cancer focus largely on prostate specific antigen (PSA). This protein is known to be a glycosylated serine protease, and is produced in relatively large quantities in the epithelial cells of the prostate and is secreted in seminal fluid. Smaller amounts are detected in the serum of healthy individuals; higher serum concentrations are thought to be correlated with pathological conditions such as prostate cancer. Other diagnostic methods address nucleic acids differentially expressed in prostate cancer.

U.S. Pat. No. 5,674,682 issued Oct. 7, 1997, to Croce et al. relates to methods for detecting prostate cancer micrometastasis, in which a sample containing nucleic acids is amplified and probed by hybridization to particular oligonucleotide probes. These probes are disclosed as being specific for prostate cancer.

U.S. Pat. No. 5,658,730 issued Aug. 19, 1997, to McGill et al., entitled "Methods of Human Prostate Cancer Diagnosis", discloses diagnostic techniques for the detection of human prostate cancer. A set of degenerate probes is used to detect gene amplification in prostate cancer cells at regions of chromosome 8q24.1-24.2. A comparison of the probe sequence with the specific primers used reveals no significant segments sharing identity between either of the specific primers and the disclosed probe. Copy number changes of chromosome 8q serve as a marker for the development of aggressive prostate cancers.

U.S. Pat. No. 5,622,829 issued Apr. 22, 1997, to King et al., entitled "Genetic Markers for Breast, Ovarian and Prostatic Cancer", discloses the nucleotide sequences for several alleles of BRCA1. The specification suggests ascertaining men at risk for prostatic cancer in view of female siblings or family members diagnosed for breast cancer. Several alleles of BRCA1 are disclosed. A method of screening a patient for prostatic cancer susceptibility based on hybridizing with nucleic acids comprising the sequences provided is also claimed.

U.S. Pat. No. 5,614,372 issued Mar. 25, 1997, to Lilja et al. relates to a bioaffinity assay of PSA using monoclonal antibodies in which a measure of PSA is related to the total of the concentration of PSA plus human glandular kallikrein-1 present in a sample of body fluid. The PSA level determined may be either the concentration of free PSA (i.e., uncomplexed PSA) or the concentration of PSA complexed with alpha-1 anti-chymotrypsin. The assay results permit discrimination between benign prostatic hyperplasia and prostate cancer.

U.S. Pat. No. 5,552,277 issued Sep. 3, 1996, to Nelson et al., entitled "Genetic Diagnosis of Prostate Cancer", teaches that prostatic glutathione-S-transferase promoter becomes hypermethylated in most prostatic cancers. Nelson et al. discloses a method of detecting the hypermethylated promoter in view of its altered susceptibility to a methylation-sensitive restriction nuclease.

U.S. Pat. No. 5,543,296 issued Aug. 6, 1996, to Sobol et al. entitled "Detection of Carcinoma Metastases by Nucleic Acid Amplification", discloses a method for detecting metastasis of a prostate carcinoma which entails treating a sample of non-prostate tissue in such a way as to amplify mRNA for PSA. A method for detecting carcinoma metastases in body tissues and fluids is disclosed only in general, broad terms; prostatic acid phosphate [sic, phosphatase] and PSA are mentioned only at col. 12, 1, 23-26. Several primers are disclosed.

U.S. Pat. No. 5,506,106 issued Apr. 9, 1996, to Croce et al., entitled "Methods of Detecting Micrometastasis of Prostate Cancer", discloses a procedure for diagnosing prostate cancer metastasis by seeking mRNA from PSA among the population of nucleated cells in a blood sample, using RT-PCR with PSA-specific primers.

U.S. Pat. No. 5,501,983 issued Mar. 26, 1996 to Lilja et al. entitled "Assay of Free and Complexed Prostate-Specific Antigen", discloses methods of immunoassay for measuring PSA both free and as a proteinase inhibitor complex.

In spite of these advances, there remains a need to develop prognostic tumor markers that can be measured in limited needle biopsies early in the progression of prostate cancer, especially in the case of aggressive prostate cancer. There further remains a need to address more selective and specific assays for various types of prostate cancer. Assays are needed that permit distinguishing prostate cancer from non-neoplastic prostate disease. Furthermore there is a need to develop diagnostic methods that facilitate identifying prostate cancers of differing aggressiveness and metastatic potential. There is likewise a need for the diagnostic probes on which such methods are founded. This invention addresses these needs.

SUMMARY OF THE INVENTION

The invention relates to a novel gene, PB39, that is up-regulated, or over-expressed, in prostate cancer. The gene has been identified by means of its cDNA obtained by reverse transcription of the corresponding mRNA. Microdissection of prostate glands that had been surgically removed from prostate cancer patients revealed a novel up-regulated transcript in an aggressive prostate carcinoma. Differential analysis for the presence of this gene was carried out from the same glands by comparing transcription in microdissected normal prostatic epithelium versus that in microdissected invasive tumor. The transcript was over-expressed in 5 of 10 prostate carcinomas examined. A variant transcript was over-expressed in 4 of 4 prostate carcinomas, and was found in only 1 of 4 normal samples.

The invention provides a purified and isolated nucleic acid that includes the sequence of PB39 given in SEQ ID NO:1 or its complement, and the sequence of the PB39 variant given in SEQ ID NO:3 or its complement. In particular embodiments, the nucleic acid may be an RNA or a cDNA. Additionally, the invention provides a purified and isolated nucleic acid, such as a primer or probe, that includes a sequence that is a fragment of the PB39 sequence or its complement, or a fragment of the PB39 variant or its complement. Examples of such primers are given in SEQ ID NO:7. SEQ ID NO:8, SEQ ID NO:10, SEQ ID NO:11, and SEQ ID NO:12.

The invention additionally provides polypeptides, whose sequences are given in SEQ ID NOs:2 and 4, that are encoded by nucleic acids that include either the sequence for PB39 or the sequence for the PB39 variant. In one embodiment, this polypeptide is a recombinantly produced polypeptide. The invention furthermore provides an antibody that binds immunospecifically with PB39 or PB39 variants.

A method of detecting precancerous cells or cancer cells in the prostate of a subject is also provided in this invention. The method includes providing a sample of tissue or fluid from the subject and determining whether the sample contains an abnormally high content of a nucleic acid that includes the sequence of PB39 given in SEQ ID NO:1 or its complement, or the sequence of the PB39 variant given in SEQ ID NO:3 or its complement, or a fragment of these sequences. A finding that the sample contains an abnormally high content of the nucleic acid indicates that the subject has precancerous cells or cancer cells in the prostate. In an important embodiment of this method, the determining step includes amplifying the nucleic acid and detecting the amplified nucleic acid.

Additionally the invention provides a method of detecting precancerous or cancer cells in the prostate of a subject. This method includes providing a sample of tissue or fluid from the subject and determining whether the sample contains an abnormally high content of a polypeptide that is the gene product of the PB39 gene or the variant PB39 gene. Finding that the sample contains an abnormally high content of the polypeptide indicates that the subject has precancerous or cancer cells in the prostate. In an important embodiment of this method, the determining step further includes contacting at least a portion of the sample with an antibody that binds immunospecifically with the polypeptide and determining the amount of the antibody that has bound with the polypeptide present in the sample. In particular embodiments of both of these methods, the sample may be a body fluid, or may be tissue originating from the prostate.

BRIEF DESCRIPTION OF THE DRAWING

FIG. 1. Panel a. Denaturing electrophoresis gel comparing reverse transcription-polymerase chain reaction (RT-PCR) amplification products produced by arbitrary and zinc finger primers. Five tumor samples (T) and two normal samples (N) from NCI Patient 1542 are shown. Two bands increased in the tumor samples are present (arrow and arrowhead). R00504 is represented by the arrow. Panel b. Denaturing electrophoresis gels showing R00504 overexpression in two cases (Table 1, cases 1 and 2). Left: RT-PCR amplification of R00504 in normal (N) and tumor (T) samples. Right: Amplification of beta-actin from the same samples. +, reverse transcriptase reaction with Moloney Murine Leukemia Virus (MMLV); −, MMLV reverse transcriptase was replaced by water; C, positive control.

FIG. 2. Northern blot of fetal tissue samples using the specific probe R00504. Lanes contain RNA as follows: lane 1, kidney; lane 2, liver; lane 3, lung; and lane 4, brain. Standards are shown on the right.

FIG. 4. Panels A and B. Nucleotide and amino acid sequence of PB39. The nucleotide sequence is numbered on the left and the amino acid sequence numbered on the right. The underlined ATG start is at nucleotide position 77. For the two sequences beginning at nucleotide position 1613, the upper nucleotide and amino acid sequences refer to the 2.3 kb transcript (SEQ ID NO:1 and SEQ ID NO:2, respectively). The lower nucleotide and amino acids sequences refer to the 5 kb transcript (SEQ ID NO:3 and SEQ ID NO:4, respectively). Panel C. Sequence overlap and divergence between 2.3 kb and 5 kb transcripts (upper and lower, respectively). Open reading frame (between arrowheads), 5' untranslated region (UTR) (vertical fine pattern), 3' UTR (area downstream of arrowhead), inserted sequence of the 5 kb transcript (black), position of divergence (arrow). The white area corresponds to the same sequence in both transcripts. Representative EST clones are identified below each transcript.

FIG. 5. Clontech fetal tissue Northern blot probed with radiolabelled 5 kb transcript specific probe. The exposure time was 5 days. The amount of RNA loaded on all of the gels was adjusted to give similar beta-actin hybridization signals and represents approximately 2 µg of poly A-selected mRNA.

FIG. 6. Regional localization of PB39. Panel A. Localization to chromosome 11p. 4'6'-Diamino 2-phenyl-indole (DAPI) counterstained metaphase showing the location of the PB39 gene (red, at arrows) on the short arm of chromosome 11. Panel B. "G-banded" chromosomal analysis. An example of the DAPI image of Panel A showing chromosome 11 which was converted to a black and white "G-band" image to show the position of PB39 on the short arm of chromosome 11 close to the centromere. The position of PB39 is identified at 11p11.1-11.2. Panel C. DAPI and simulated G-banded image of chromosome 11 after fluorescence in situ hybridization (FISH). Arrows show location of PB39. Panel D. Ideogram of chromosome 11.

DETAILED DESCRIPTION OF THE INVENTION

Figure 3A:
FIG. 3. Panel A. Clontech adult tissue Northern blots probed with radiolabelled R00504 insert. The exposure times of the blots on the left and right were 40 hrs and 6 hrs, respectively. Panel B. Clontech fetal tissue Northern blot probed with radiolabelled R00504 insert. The exposure time was 40 hrs.

The gene designated PB39 identified in the present invention includes a nucleotide sequence previously found in expressed sequence tag (EST) R00504 (GenBank). The procedure that led to its discovery and identification depends on an analysis of differential transcription of the gene in neoplastic tissue from a prostate gland that is cancerous compared to normal tissue from the same gland. Specifically, microdissection of epithelial tissue from prostate glands that had been surgically removed from prostate cancer patients was carried out. PB39 in microdissected invasive tumor compared to that in microdissected normal prostatic epithelium was found to be over-expressed in 5 of 10 prostate carcinomas examined. These findings identify the condition detected as prostatic intraepithelial neoplasia, the earliest precursor of prostate cancer. Reliable evaluation of overexpression was aided by comparing transcription to that of the constitutively expressed gene for beta-actin.

The finding that PB39 is over-expressed in prostatic intraepithelial neoplasia indicates that the gene and its gene product are useful in the early diagnosis of this disease, and that they may serve as a marker for its early appearance. Methods that may be employed for this purpose include, without limiting the scope of the invention, assay for the gene by the polymerase chain reaction and in situ hybridization, and analysis for the protein product by immunoassay, or by immunohistochemical detection such as indirect immunofluorescence. Probes and antibody reagents may be developed to permit imaging prostate cancer, both primary and metastatic. Isolation of the PB39 gene and gene product will contribute to the understanding of prostate cancer development and progression, based on experimental studies using methods such as immunohistochemistry or in situ hybridization. The availability of PB39 will additionally permit the development of methods of treatment of subjects determined to have prostate cancer. Specifically, treatment modalities such as chemotherapy, immunotherapy, or anti-sense nucleotides, for example, may be developed to target the prostate cancer identified by PB39. The gene may be applied to produce the recombinant gene product in appropriate host cells, especially in mammalian cells. The recombinant gene product then may serve as the immunogen to provide antibodies to be applied in the various methods mentioned above.

Initial identification of PB39 has been made as a result of experiments performed on surgically excised cancerous prostate glands. The glands were frozen in liquid nitrogen as rapidly as possible in order to preserve all metabolically unstable species that may be present as well as possible without breakdown. Particular species of interest in the present invention are actively transcribed mRNA species leading to expression of genes that may be characteristic of the cancerous state. RNA was extracted from microdissected invasive tumor cells and from corresponding normal prostatic epithelium from the same gland, and the gene expression profile was examined in the two sets of cells as they exist in vivo.

Microdissection was carried out on sections of the prostate under low power microscopic magnification with sufficient resolution and care to isolate only the types of tissue desired (Chuaqui, R. et al., Identification of a Novel Transcript Up-Regulated in a Clinically Aggressive Prostate Carcinoma, Urology 50: 302-307 (1997), incorporated herein by reference). In addition to the microscopic field visualized, guidance was further obtained from adjacent sections that have been treated and stained to enhance the identification of histological features. The dissection procedure was carried out as rapidly as possible in order to minimize degradation of RNA species by endogenous processes. The microdissection technique is further characterized in Emmert-Buck et al. (Increased gelatinase A and cathepsin B activity in invasive tumor regions of human colon cancer samples, Am J Pathol 145:1285-1290 (1994)) and Zhuang et al. (A microdissection technique for archival DNA analysis of specific cell populations in lesions <1 mm in size, Am J Pathol 146:620-625 (1995)) both of which are incorporated herein by reference.

Each sample of microdissected tissue is then extracted with a procedure, such as the guanidinium thiocyanate-phenol-chloroform method (Chomczynski et al., Single-step of RNA isolation by acid guanidinium thiocyanate-phenol-chloroform extraction, Anal Biochem 162: 156-159 (1987)), in order to provide an RNA sample that may be assessed for the presence of genes of interest. The samples should contain sufficient numbers of cells to provide RNA for the subsequent manipulations. Commonly it is expected that at least about 5,000 cells, and preferably at least about 10,000 cells will be treated for a given sample. If necessary, further purification of the isolated RNA may be carried out. This may include, without intending to limit the purification methods employed, steps such as digestion with deoxyribonuclease, and further purification steps known to workers of skill in cell biology, molecular biology, and cancer research that permit one to isolate mRNA that is actively involved in translation of genes to yield protein products. Such methods are set forth in general in "Current Protocols in Molecular Biology", Ausubel et al., John Wiley and Sons, New York 1987 (updated quarterly), and "Molecular Cloning: A Laboratory Manual", 2nd Ed., Sambrook, Fritsch and Maniatis, Cold Spring Harbor Laboratory, Cold Spring Harbor, N.Y., 1989, which are incorporated herein by reference.

The purified mRNA sample is then reverse transcribed to yield the corresponding cDNA species using procedures well known to workers of skill in cell biology, molecular biology, and cancer research (Ausubel et al., Sambrook et al.). The cDNA sample is then further analyzed for species that contain sequence motifs known to bind DNA, such as zinc finger motifs. This is carried out by using PCR with primers designed to amplify the motifs sought. In particular, the present invention discloses that one such primer is an arbitrary primer developed by Stratagene (La Jolla, Calif.), primer A2 (AATCTAGAGCTCCAGCAG (SEQ ID NO:5)), and a zinc finger-directed primer (Zinc 2, GTCGTCGAATTCCACACAGGAGAAAAGCC (SEQ ID NO:6: Stone et al., Targeted RNA fingerprinting: the cloning of differentially-expressed cDNA fragments enriched for members of the zinc finger gene family, Nucl Acids Res 22: 2612-2618 (1994)).

This PCR generally provides an amplified DNA sample enriched in DNA molecules encoding gene products having zinc finger motifs. The present inventors discovered unexpectedly that differential display gels of PCR products obtained using this primer pair yielded a particular band having pronounced expression in prostatic cancerous epithelium but not in normal epithelium. Upon partial sequencing of this DNA, it was found that a portion of the sequence matched a sequence appearing in the EST database, GenBank accession no. R00504.

Primers specific for R00504 were designed. These are GCATGTTACAGGTAGAAAAGCC (SEQ ID NO:7) and CTGGCGTATCTGAAGAGTCTG (SEQ ID NO:8).

These primers may be employed for specific binding to and amplification of sequences contained within R00504, and as such are useful in probing the gene overexpressed in cancerous epithelium. When these R00504-specific probes were labeled and employed in Northern blot analysis of mRNA species from prostatic epithelium samples, a molecule of approximately 2.6 kb was identified. The gene defined in this mRNA transcript is termed PB39. The complete nucleotide sequence for PB39 has been obtained and is provided in SEQ ID NO:1. The sequence of the protein encoded by PB39 is provided in SEQ ID NO:2. The details of the procedures used to obtain this result are provided in Example 6.

It was subsequently determined that a variant of PB39 results from an alternative RNA splicing mechanism during maturation of the RNA transcript. This variant was analyzed by PCR, including using a probe specific for the sequence inserted into the long form. Sequencing of the resulting amplified DNA showed the variant to have a different sequence, and a termination codon yielding a translated gene product one amino acid residue longer than the 2.6 kb form. The nucleotide sequence of the variant PB39 up to its termination codon is provided in SEQ ID NO:3, and the sequence of the protein encoded by this variant is given in SEQ ID NO:4. The details of these procedures and of the results obtained are provided in Example 7.

The transcripts corresponding to SEQ ID NOs:1 and 3 are found to occur in abnormally high concentrations in samples derived from cells of prostate cancer epithelium when referred to the level found in cells from normal epithelium from the same prostate gland. This observation forms the basis of a method of detecting precancerous cells or cancer cells in the prostate of a subject. The level of PB39 transcript is determined, for example, by using reverse transcription-PCR, Northern blot analysis, or comparable methods known to workers of skill in cell biology, molecular biology, and cancer research. In these methods, the PCR may be carried with any primer pair specific for PB39, including but not limited to, primers that contain the sequences of SEQ ID NOs:7, 8, 10, 11, and 12. The probes to be applied in Northern blot analysis are to be labeled, and may be based on the primers including the sequences of SEQ ID NOs:7, 8, 10, 11, and 12 mentioned above, as well as on labeled forms of nucleic acids containing the PB39 sequences given by SEQ ID NOs:1 and 3 or their complements. The probes for Northern analysis may also employ fragments of the PB39 sequences given by SEQ ID NOs:1 and 3 or their complements, with the proviso that such fragments are specific for PB39 and are long enough to hybridize effectively with the target sequence in the sample being probed. In each case, the levels of the PB39 transcripts are normalized by taking the ratio of the level of the transcript found to the level of the transcript for a constitutive gene present in the same cells. An example of a gene for a constitutively expressed transcript is that for beta-actin. The present invention also provides diagnostic kits including the above novel nucleic acids, primers and probes for purposes of carrying out this method of detection.

The method of detecting precancerous or cancer cells determines whether the level of PB39 transcript is present at an abnormally high level. An "abnormally high" level, or content, of the nucleic acid transcript, as used herein, relates to a ratio of the level of PB39 transcript to the level of beta-actin transcript that is preferably about two times or more higher in the sample of the cancerous epithelium than that found in a set of samples taken from normal epithelium, as expressed by a mean value found therein.

In performing this method, the sample from the subject may be a biopsy sample drawn from the prostate gland of the subject. In favorable cases, such a biopsy may be obtained in a procedure that minimizes invasiveness and discomfort to the subject, such as a needle biopsy. Alternative samples may be a body fluid from the subject, including but not limited to, blood, urine, and seminal fluid. Generally, sampling methods and choices are well known to workers of skill in the art such as urologists and oncologists.

The gene products encoded by the nucleotide sequences of SEQ ID NOs:1 and 3 are provided in SEQ ID NOs:2 and 4, respectively. The proteins incorporating these amino acid sequences may be produced as recombinant proteins in host cells modified by vectors containing nucleic acid sequences, such as the sequences of SEQ ID NOs:1 and 3, that encode the proteins. Such recombinant proteins may be produced in prokaryotes such as *Escherichia coli*. Preferably, however, eukaryotic hosts will be employed. For example, host cells from members of many families of Lepidoptera, such as SF-9 cells, may be employed.

Such host cells are modified to produce the desired protein by infection with a recombinant baculovirus. *Autographa californica*, wherein the recombinant baculovirus carries the gene for the heterologous protein, commonly under the control of the promoter for the gene for the polyhedrin protein of the virus.

Alternatively, various mammalian cells may be used to produce the PB39 protein product upon being transfected with an appropriate vector harboring the gene including the sequence of SEQ ID NO:1 or SEQ ID NO:3. Methods for preparing the vectors and producing the recombinant proteins are set forth broadly in general terms in Ausubel et al. and Sambrook et al., for example. These procedures are well known to workers of skill in the fields of cell biology and molecular biology. The PB39 protein is to be produced as a recombinant protein in a system such as summarized herein, or an equivalent system, and purified to a high degree of purity. Procedures that may be employed in the purification include fractional precipitation, chromatography, centrifugation, and the like. Such procedures are well known to workers of skill in protein chemistry and enzymology and are, for example, set forth in Deutscher, M. P. (ed.), Guide to Protein Purification: Methods in Enzymology, Vol. 182, Academic Press, San Diego, Calif., 1990; and Scopes, R. K., Protein Purification: Principles and Practice, 3rd Ed., Springer-Verlag, New York, N.Y., 1993.

The purified PB39 protein corresponding to SEQ ID NO:2 or SEQ ID NO:4 may be used as the immunogen to prepare antibodies against the respective proteins. The antibody may be a polyclonal antibody, obtained upon immunizing a host such as a rabbit with the PB39 immunogen. Alternatively, one or more monoclonal antibodies may be obtained upon immunizing a host such as a mouse with the PB39 immunogen, and preparing hybridomas that secrete the antibody. Successful hybridomas are obtained as a result of probing hybridoma clones for antibody molecules that bind immunospecifically with the PB39 immunogen. These procedures are well known to workers of skill in the field of molecular immunology, and are set forth in general terms in Harlow and Lane, "Antibodies: A Laboratory Manual", Cold Spring Harbor Laboratory Cold Spring Harbor, N.Y. (1988), and Coligan, J., A. Kruisbeek, D. Margulies, E. Sevach, and W. Strober. "Current protocols in immunology", John Wiley & Sons. New York (1994), which are incorporated herein by reference.

Antibodies produced according to the procedures described above are useful in immunoassays directed to detecting precancerous cells or cancer cells in the prostate of a subject. In such immunoassays, for example in an enzyme linked immunosorbent assay (ELISA), the concentration of PB39 antigen is detected in a sample obtained from the subject. If the sample is a fluid sample, it may be used as is, or treated to remove cellular components, and furthermore may be volumetrically diluted if necessary to attain an appropriate concentration of the antigen. If the sample is a sample of cells from the prostate gland the sample may be homogenized and the fraction containing the PB39 antigen may be concentrated. If desired, the prostate sample may be microdissected first to provide prostate epithelium. In an ELISA, by way of nonlimiting example, a first antibody that binds immunospecifically with PB39 is immobilized on the surface of a suitable assay vessel, and the remaining surface sites are then blocked with an innocuous protein. The sample suspected of containing PB39 antigen is added and allowed to react with the immobilized first antibody. After thorough rinsing, any immobilized antigen is further treated with a second antibody that binds immunospecifically with PB39, and the second antibody is detected. These procedures are well known to persons of skill in the fields of molecular immunology and diagnostic immunochemistry.

The method of detecting precancerous cells or cancer cells determines whether the level of PB39 antigen is present at an abnormally high level. An "abnormally high" level, or content, of the antigen, as used herein, relates to the level of PB39 antigen that is, preferably, about two times or more higher than that found in a set of samples taken from normal subjects, as expressed by a mean value found therein. These levels or contents may vary, depending on the origin of the particular sample taken. In one embodiment, the level or content is determined as an absolute number representing the concentration or amount of the antigen present in the sample taken. In another embodiment, the level or content of PB39 antigen may be related by ratio to the level or content of a second antigen known to be constitutively present in the particular sample used for the assay. In this embodiment, the value of the ratio of the level of PB39 antigen to the level of the constitutive antigen is considered to be "abnormally high" when it is preferably about two times or more higher than the ratio found in a set of samples taken from normal subjects or from normal cells, as expressed by a mean value found therein. The present invention also provides diagnostic kits including the above novel antibodies for purposes of carrying out this method of detection.

The predicted N-terminal sequence of the PB39 protein, as shown in SEQ ID NOs:2 and 4, suggests the presence of a signal-recognition particle sequence for a secreted protein. If the PB39 protein is in fact secreted, its concentration may be increased in the serum early in the progression of prostate cancer, in prostatic intraepithelial neoplasia (PIN) for example. Identification of a serum protein characteristic of prostate cancer would be a useful tool for the early detection of this disease. Epidemiologic studies have shown that PIN precedes the development of prostate cancer by several decades in most men. Thus a marker of early malignancy could identify those men who develop PIN lesions early in life and are at greatest risk for developing clinically significant disease (Bostwick, D. G. et al., Molecular biology of prostatic intraepithelial neoplasia, Prostate, 29: 117-134 (1996)).

The PB39 gene described in the present invention is in general dysregulated in disease states such as prostate cancer. It may be subject to altered expression (i.e., overexpression or underexpression) and/or altered processing, resulting in a change in the level of the expressed protein in such a disease state.

EXAMPLES

Example 1

Microdissection of Cancerous Prostate Glands and Isolation of RNA

Patient samples. All tissue samples were obtained from radical prostatectomy specimens from either the Mayo Clinic (Rochester, Minn.) or the National Cancer Institute (NCI) (Bethesda, Md.). Samples were snap-frozen within minutes after surgery and stored at −70° C. until use. Unstained 12-μm frozen tissue sections were dissected under microscopic visualization as previously described (Emmert-Buck M. et al., Increased gelatinase A and cathepsin B activity in invasive tumor regions of human colon cancer samples, Am J Pathol 145: 1285-1290 (1994); Zhuang Z. et al., A microdissection technique for archival DNA analysis of specific cell populations in lesions <1 mm in size, Am J Pathol 146: 620-625 (1995)). Essentially pure populations of normal epithelium and invasive tumor were dissected in each case. An adjacent hematoxylin and eosin-stained section was used as a guide to ensure accuracy of dissection. All dissections were completed within 30 minutes of preparation of the frozen tissue sections.

RNA Isolation. Approximately 5000 to 10,000 normal epithelial or tumor cells were microdissected for each sample. A scaled down version of the Stratagene (La Jolla, Calif.) RNA Microisolation procedure was used to isolate RNA (Chomczynski P. et al. Single-step RNA isolation by acid guanidinium thiocyanate-phenol-chloroform extraction. Anal Biochem 162: 156-159 (1987)). After resuspension of the RNA pellet, a DNAse step and re-extraction was performed using the MessageClean™ kit from GenHunter (Nashville, Tenn.) according to the manufacturer's instructions.

Example 2

Reverse Transcription and Polymerase Chain Reaction Amplification of the Prostate-Specific Transcript Complementary DNA (cDNA) was obtained by reverse transcription (RT) using the RNAamp™ kit from GenHunter except that 2.5 μM random hexamer primers from Perkin-Elmer (Norwalk, Conn.) were used instead of the primers supplied. The final mixture was treated as follows: 65° C. for 5 minutes, 25° C. for 10 minutes, then 1 μL of Moloney Murine Leukemia Virus with reverse transcriptase activity (MMLV) (GenHunter) was added and incubated at 25° C. for 10 minutes, 37° C. for 40 minutes, and 94° C. for 5 minutes. Each RT reaction generated about 20 μL solution containing about 0.5-1 ng of cDNA. For each RNA sample, a negative control was done for the RT reaction, replacing the MMLV with 1 μL of water.

Arbitrary Zinc Finger Polymerase Chain Reaction (PCR). Several PCR reactions utilizing arbitrary primers from the RAP-PCR kit from Stratagene and degenerate zinc finger primers (Stone B. et al., Targeted RNA fingerprinting: the cloning of differentially-expressed cDNA fragments enriched for members of the zinc finger gene family. Nucl Acid Res 22: 2612-2618 (1994)) were run to assess differences in gene expression between normal epithelium and invasive tumor in NCI patient 1542 (Table 1, case 2; see Example 3). PCR conditions were systematically varied to maximize the reproducibility of bands present on denaturing electrophoresis gels. The specific PCR primers that generated expressed sequence tag (EST) clone R00504 (see below) were: Primer 1: Stratagene arbitrary primer A2,

AATCTAGAGCTCCAGCAG (SEQ ID NO:5), and Primer 2: zinc 2,

GTCGTCGAATTCCACACAGGAGAAAAGCC (SEQ ID NO:6).

PCR conditions were: 1 cycle of 94° C. for 2 minutes, followed by 35 cycles of 94° C. for 30 seconds, 50° C. for 30 seconds, 72° C. for 1 minute, and 1 cycle of 72° C. for 10 minutes.

Gel Electrophoresis. Labeled amplified DNA was mixed with an equal volume of formamide loading dye (95% formamide; 20 mM ethylenediaminetetraacetic acid; 0.05% bromophenol blue, and 0.05% xylene cyanol). The samples were denatured for 5 minutes at 94° C. and loaded onto a gel consisting of 6% acrylamide (49:1 acrylamide/bis). Bands in the gels were transferred to 3-mm Whatman paper, the paper was dried, and autoradiography was performed with Kodak X-OMAT film.

Results. Normal prostatic epithelial and tumor RNA samples from NCI patient 1542 (Table 1, case 2; see Example 3) were analyzed by the low-stringency RT-PCR procedure outlined above using arbitrary and zinc finger primers. Several parameters, including the identities of the RT primers and PCR primer sets (sizes and sequences), as well as reaction conditions, were varied in an attempt to elicit differences in gene transcription between normal and tumor cells. In general, comparison of normal and tumor samples produced identical patterns of gene expression; several hundred PCR products were observed that did not vary between normal and tumor cells.

However, PCR with primers A2 (SEQ ID NO:5) and zinc 2 (SEQ ID NO:6) resulted in the presence of a strong product selectively in the tumor sample (FIG. 1, Panel A). Separate PCR reactions in which only one of the primers was used did not produce a similarly sized band. The band was extracted from the gel, reamplified, and subjected to partial sequencing. Direct sequencing was performed using the Amplicycle™ sequencing kit from Perkin-Elmer according to the manufacturer's instructions. The following 103-base pair (bp) sequence was obtained:

5' ACAGGAATCC CCAGGAGTGA AGAATAAGCA GGAGGCCCCA GATTCACCTT TAGGGCAAGG AGAGAGAAAC AGAGTCAAGT AGGTAGTCAT CTGCCCTTAA GCC 3' (SEQ ID NO:9).

Analysis showed a match of 102 bp out of the 103 bp to a gene sequence in the expressed sequence tag (EST) database (GenBank accession R00504).

The patient from whom this sample was obtained was a 47-year-old black man who first presented with localized (Stage T2A) prostate cancer. Histopathologic examination of the prostatectomy specimen showed a poorly differentiated adenocarcinoma (Gleason score 8). The patient was clinically free of disease until 1 year postoperatively, when he developed rapidly rising prostate-specific antigen levels and clinical evidence of recurrent disease.

Example 3

Analysis of Differential Expression of R00504

Messenger RNA levels of R00504 were determined in normal prostate epithelium and corresponding invasive tumor cells from a test panel of 10 prostate carcinoma samples (total of 20 samples. Total RNA was recovered from each sample, treated with DNAse, and R00504 was amplified by RT-PCR. The level of the beta-actin gene from each sample, likewise obtained by RT-PCR, was used as an internal standard to quantitate R00504 levels. For the PCR of the beta-actin gene, 1 μL of the cDNA sample was subjected to PCR with specific primers from Clontech (Palo Alto, Calif.) according to the manufacturer's instructions. All reactions were run at least twice to ensure reproducibility of results, and a control reaction without reverse transcriptase was run in parallel for all normal and tumor samples.

To analyze differential expression, R00504-specific primers were used:

Primer 1=GCATGTTACAGGTAGAAAAGCC (SEQ ID NO:7);

Primer 2=CTGGCGTATCTGAAGAGTCTG (SEQ ID NO:8).

PCR conditions using these primers were as follows: 1 cycle of 94° C. for 2 minutes, followed by 35 cycles of 94° C. for 30 seconds, 60° C. for 1 minute, 72° C. for 1 minute, and 1 cycle of 72° C. for 10 minutes. Beta-actin and R00504 PCR reactions included dilutions of samples to ensure that reactions were not at saturation conditions. All reaction sets were run a minimum of two times to ensure reproducibility of results, and samples were run in parallel with a negative reverse transcriptase control. Overexpression of R00504 was determined visually and was considered to be present when R00504 was selectively expressed in tumor cells or substantially increased in tumors compared with beta-actin expression (FIG. 1).

Normal prostatic epithelium and corresponding invasive tumor were microdissected from a test panel of 10 prostate carcinoma samples. Using the specific R00504 PCR primers given by SEQ ID NOs:7 and 8, samples from NCI patient 1542 showed strong expression of R00504 in the tumor sample but no expression in the normal epithelial sample, consistent with the initial experiment utilizing primers A2 and zinc 2 (SEQ ID NOs:5 and 6; see Example 2).

Table 1 presents the results obtained probing the ten patient samples for R00504. Five of the patients in the test panel showed substantial overexpression of R00504 in the tumor samples (Table 1, cases 1, 2, 6, 9, 10). FIG. 1. Panel B shows examples of two cases demonstrating tumor-specific increases in R00504 levels. Case 1 shows expression of R00504 in both the normal and tumor samples, with a relative increase in expression in the tumor. Case 2 shows selective expression in the tumor sample. Overexpression of R00504 in normal cells relative to the corresponding tumor was not observed in any of the cases. These results indicate that R00504 overexpression occurs frequently in prostate cancer. The clinical parameters of the tumors varied among patients (Table 1), and no correlation between R00504 expression and clinical features of the tumors was found. However, the majority of the samples was from patients who had undergone surgery only a short time prior to these studies, so that minimal follow-up data are available.

Example 4

Northern Blot Analysis of R00504 Transcription

Northern blots were performed to assess the size of the transcript in tissues. In order to serve as a probe, R00504 was amplified and labeled by PCR with sequence-specific primers using $^{32}$P-deoxycytidine triphosphate and the PCR conditions described in Example 3. The labeled PCR product was used to probe samples from various human fetal tissues (obtained from Clontech) according to the manufacturer's recommendations. Two million counts per minute per milliliter of hybridization solution was applied.

The Northern blots containing RNA from fetal kidney, liver, lung, and brain tissues showed a single band of approximately 2.6 kilobases (FIG. 2). Expression was highest in the fetal liver sample, consistent with the fact that the initial identification of the R00504 EST used a cDNA library from fetal liver.

The full gene represented by the RNA identified in this Example, and which contains the nucleotide sequence provided in Example 2 as part of EST R00504, is termed PB39 herein.

Example 5

Northern Blot Analysis for PB39 in Adult and Fetal Human Tissues

Figure 3B:
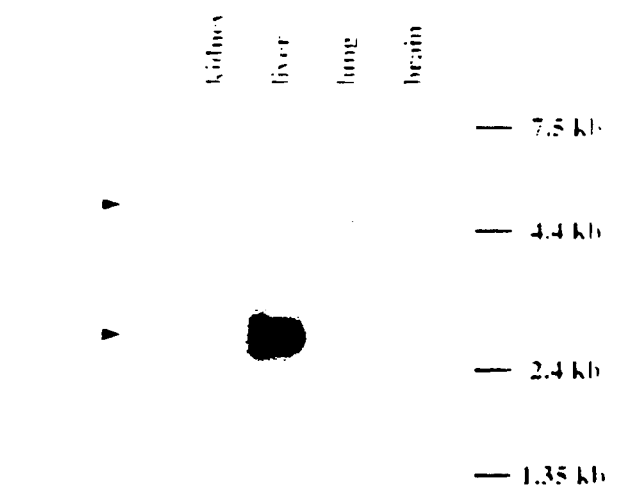

Northern blot analysis using labeled R00504 as a probe showed a transcript of approximately 2.6 kb which was expressed in tissues of the adult colon, small intestine, ovary, prostate, spleen, and pancreas (FIG. 3, Panel A), fetal kidney, liver, and lung (FIG. 3. Panel B), and adult liver and skeletal muscle (results not shown). The level of expression was highest in adult pancreas tissue (FIG. 3, Panel A).

Example 6

Nucleotide Sequence of PB39

To determine the complete nucleotide sequence of the PB39 cDNA, specific 5' and 3' PB39 primers were generated and used to isolate PB39 specific PCR products from a human pancreas cDNA library using the Rapid Amplification of cDNA Ends (RACE) method (Marathon-Ready cDNA. Clontech). The 3' and 5' PB39 RACE primer sequences GACCGCATAGACTTCTCAGA (SEQ ID NO:10) and GCATGTTACAGGTAGAAAAGCC (SEQ ID NO:7), respectively, were chosen from EST clone R00504. A 700 bp 3' fragment and a 2 kb 5' fragment were produced, subcloned into a plasmid PCR vector, and cycle sequenced. To validate the sequence, gene-specific PCR products amplified from the pancreas library were directly sequenced, and verified by 10 independent sequencing reactions. Assembly of the entire set of sequences produced a 2317 nucleotide cDNA sequence (SEQ ID NO:1) that includes 76 nucleotides of 5' untranslated sequence, a 1677 nucleotide open reading frame (559 amino acids), and 564 nucleotides of 3' untranslated sequence (FIG. 4, Panels A and B). The consensus Kozak sequence GCCGCCATGG placed the translation initiation methionine at nucleotide position 77 (Kozak M., Structural features in eukaryotic mRNAs that modulate the initiation of translation, J Biol Chem 266: 19867-19870 (1991)).

Example 7

Nucleotide Sequence of a Variant of PB39

Basic Local Alignment Search Tool (BLAST) analysis (Altschul, S. F. et al., Gapped BLAST and PSI-BLAST: A new generation of protein database search programs, Nucleic Acids Res 25:3389-3402 (1997)) of the PB39 sequence against the human EST database showed multiple PB39 EST clones from diverse tissue types. Interestingly, several PB39 homologous clones showed an identical divergence within the coding sequence at nucleotide 1610 (FIG. 4, panel B) with introduction of an additional nucleotide sequence. To analyze this longer, alternative form of PB39 further, a PCR primer specific for the inserted sequence (TCTGCAAAGTGGCTGAGATGAG (SEQ ID NO:11)) was designed and used to amplify cDNA from the pancreas library, together with a PB39-specific 5' primer (CCTGC-CTTATCTTTCTGAACTGCACC (SEQ ID NO:12)). The amplified product was isolated and directly sequenced. The sequence is shown in FIG. 4, panels A and B (SEQ ID NO:3). Analysis of the open reading frame shows the addition of 48 new amino acids beginning at nucleotide position 1613, followed by a stop codon. Thus, the larger transcript of PB39 encodes a 560 amino acid protein in which the 47 C-terminal amino ac ids found in the 2.3 kb PB39 are replaced by 48 new amino acids (FIG. 4, panels A and B). A schematic diagram of the relationship between the two RNA species is shown in FIG. 4, Panel C.

Northern blot analysis using a probe specific for the inserted sequence showed a 5 kb PB39 transcript expressed in adult pancreas and fetal liver tissue. As expected, this probe did not hybridize to the 2.6 kb PB39 (FIG. 5). A longer exposure of the R00504-probed blots did reveal a less intense transcript at 5 kb, which would be expected since this sequence is common to both transcripts (FIG. 3, panels A and B).

RT-PCR analysis was performed to study the expression of the 5 kb PB39 transcript in human prostate tissue as described above (Example 3). RT-PCR using primers directed against the inserted sequence in microdissected normal and invasive prostate epithelium showed a product in 4 of 4 tumor samples, but only 1 of 4 corresponding normal samples (results not shown). One of the cases over-expressing the 5 kb transcript did not show over-expression of the 2.6 kb form of PB39. Since the results

TABLE I

Clinical and histopathologic aspects of test panel of prostate cancer cases

| Case No./Age (yr) | R00504 | Gleason Score* | Tumor Stage* | PSA Level (ng/mL)* |
|---|---|---|---|---|
| 1/66 | ++ | 4/4 | T2A | 2.2 |
| 2/47 | ++ | 4/4 | T2C | 14.3 |
| 3/55 |  | 4/3 | T3C | 49.8 |
| 4/66 |  | 2/3 | T2C | 6.3 |
| 5/65 |  | 3/3 | T2C | 11.1 |
| 6/68 | ++ | 4/4 | T3A | 7.1 |
| 7/68 |  | 4/3 | T3A | 49.2 |
| 8/54 |  | 4/4 | T1C | 7.7 |
| 9/64 | ++ | 4/3 | T3A | 14.1 |
| 10/51 | ++ | 3/3 | T2B | 14.9 |

Key: ++ = increased levels of R00504 in invasive tumor compared with corresponding normal epithelium.
*At diagnossis.

in Table 1 show overexpression of PB39 in 5 of 10 tumor samples, it appears that both the 2.6 kb and 5 kb forms of PB39 are up-regulated in unique subsets of tumors. The physiological significance of this finding is not yet clear.

The 5 kb PB39 variant transcript was found to match EST clones primarily from fetal and tumor tissue libraries (FIG. 4, panel C). This transcript was also found to be highly expressed in a cDNA library from a microdissected prostatic intraepithelial neoplasia focus which was sequenced as part of the Cancer Genome Anatomy Project. Thus, PB39 represents one of the first identified genes whose expression has been shown to be increased early in prostate cancer development. The cellular regulation of PB39 mRNA splice variants their precise expression levels during prostate tumorigenesis, and the functional significance of altering the C-terminal 47 amino acids remain to be determined.

Example 8

Localization of PB39 on Chromosome 11

A Whitehead Institute Sequence Tagged Site marker WI-17004 (GenBank acc. G22380) maps PB39 to 291.1 cR from the telomere of the short arm of chromosome 11 (Schuler G D, Sequence mapping by electronic PCR, Genome Res 7: 541-550 (1997)). To confirm this result, in situ hybridization was performed following protocols previously described (Pinkel, D. et al., Fluorescence in situ hybridization with human chromosome-specific libraries: detection of the trisomy 21 and translocations of chromosome 4, Proc Natl Acad Sci USA. 85:9138-9142 (1988); Hirai, M. et al., A method for simultaneous detection of fluorescent G-bands and in situ hybridization signals, Cytogenet Cell Genet 66: 149-151 (1994)). The chromosomal localization of the gene was determined by hybridization of the 2 kb 5' RACE PCR product to metaphase chromosomes and converting DAPI banding to "G-banding" using IP Lab Spectrum™ (Scan Analytics, Fairfax, Va.) software for chromosomal identification. This result indicates that the PB39 gene maps to human chromosome 11p11.1-11.2. A total of 50 cells was examined to determine the precise chromosomal location of the probe. In all metaphases scored, clear signals were seen on the short arm of chromosome 11 (FIG. 6, panels A and B). DAPI banding unambiguously showed the position of the signal in the region 11p11.1-11.2 (FIG. 6, panels A, B, C and D). Both the STS primers and the fluorescence in situ hybridization (FISH) probe were directed against sequences common to the 2.6 kb and 5 kb transcripts. In both cases hybridization to only one chromosomal location was identified. Interestingly, the human chromosome 11p11-11p12 region has been postulated to harbor one or more metastasis suppressor genes, including KAI1, and has also been shown to be deleted in 70% of advanced prostate cancers (Dong. J. T. et al., KAI1, A metastasis suppressor gene for prostate cancer on human chromosome 11p11, Science 268:884-886 (1995); Kawana, Y. et al., Location of KAI1 on the short arm of human chromosome 11 and frequency of allelic loss in advanced prostate cancer, Prostate, 32: 205-213 (1997)).

Example 9

Expression of PB39 in COS Cells

A cDNA encoding PB39 is to be ligated into a vector that can be used to transfect a mammalian cell. In particular, SV40 vectors may be employed for this purpose. The PB39 gene is to be subcloned into an appropriate plasmid such that suitable restriction sites become available. The cDNA is then to be extracted using the appropriate restriction enzyme, and ligated into a complementary site in the SV40 genome.

The recombinant SV40 is to be used to transfect, for example, simian COS cells. The vector is combined with calcium phosphate for incorporation into the cells. Amplification using vectors incorporating the drug resistance gene dhfr permits larger amounts of the cloned gene to accumulate upon exposure of the culture to methotrexate, and to be expressed in the cultured cells. Upon completion of the selection, the amplified cells are to be cultured to produce the recombinant PB39 gene product.

PB39 protein is to be isolated and purified from the cultured cells. The cells are to be harvested, and gently disrupted to release the cellular contents into the medium. PB39 is to be purified using known methods including differential centrifugation, and various forms of column chromatography, such as ion exchange, hydrophobic interaction, and size exclusion. Purity is to be assessed using analytical chromatographic procedures, sodium dodecyl sulfate-polyacrylamide gel electrophoresis and/or like procedures.

Example 10

Production of Polyclonal Anti-PB39 Antibodies

Putative epitopic peptide sequences were synthesized in order to elicit polyclonal antibodies specific for PB39. Peptides common to both the 2.6 kb encoded protein and the variant transcript protein are:

peptide 644: Thr Gln Asp Glu Gln Arg Arg Trp Pro Gly Cys Asp Gln Gln (SEQ ID NO:13), peptide 645: Glu Asn Leu Pro Glu Arg Ser Val Pro Leu Arg Lys Ser Leu (SEQ ID NO:14), and peptide 646: Arg Pro Arg Tyr Cys Lys Ile Gln Lys Leu Thr Asn Ala(SEQ ID NO:15).

A peptide sequence specific for the 2.6 kb encoded protein is peptide 655: Ala Asn Gly Met Gly Pro Leu Lys Val Leu Ser Gly Ser (SEQ ID NO:16).

A peptide sequence specific for the variant transcript protein is peptide 656: Ala Arg Gly Thr Ser Glu Val Ser Asn Leu Gln Val Ser (SEQ ID NO:17).

Rabbits were immunized with a BSA conjugate of each of the above peptides, using complete Freund's adjuvant. Immunizations were done every two weeks. The rabbits were bled prior to the immunizations and again during the intervals between injections.

The anti-peptide antibody sera were affinity purified over the corresponding peptide-conjugated Affi-Gel 10™ columns. After desorption from the column, the antibody-containing eluates were concentrated for storage and use.

Figure 7:
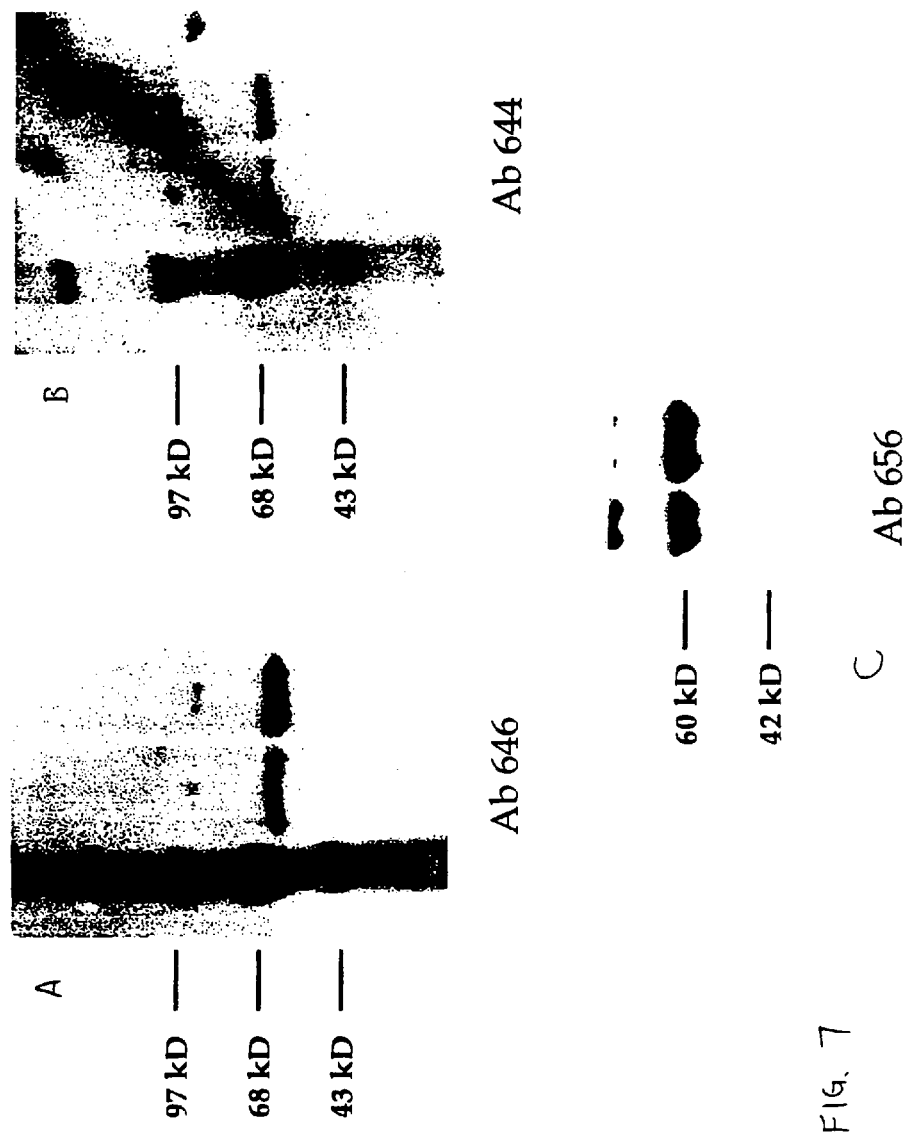
FIG. 7. Western blots of PB39 probed with polyclonal antibodies raised against peptides 646 (Panel A), 644 (Panel B) and 656 (Panel C).

The binding of the resulting antibodies was assessed in western blots. For testing of antibodies raised against peptides 655 and 656 30 µg of protein extracted from a prostate cancer cell line (1542/8.4 clone) were analyzed. For testing of antibodies raised against peptides 644, 645 and 646, protein extracted from roughly 24,000 cells from microdissected tumor samples were analyzed. Proteins were separated on a 8-12% gradient P.A.G.E. gel (NOVEX) run in tris glycine and transferred to a PVDF membrane. The membranes were blocked and incubated overnight at 4° C. with varying titers of the anti-peptide antibody mixtures (range from 1:10 to 1:5000, volume/volume). The membranes were washed and incubated with an HRP conjugated goat antirabbit secondary antibody. After washing, the membranes were incubated with a chemiluminescence substrate and visualized on X-OMAT film. For all antibodies tested, a 60 kD band was evident. This corresponds to the size anticipated for both the 2.6 kb encoded protein and the variant transcript. In FIG. 7, Panels A, B, and C, show the results obtained with the anti-646-644 and -656 antibodies, respectively. For the westerns probed with anti-655 and -645 antibodies, the bands were present, but were too faint to reproduce in a photograph. Antibody specificity was demonstrated by eliminating the bands upon competition with increasing concentrations of the corresponding epitopic peptide.

Example 11

Monoclonal Antibodies

Purified PB39, or BSA-conjugated peptides 646, 644 or 656, are to be injected into mice together with Freund's complete adjuvant. Subsequently spleen cells obtained from the mice are to be fused with immortalized murine tumor cells to produce hybridomas. Each hybridoma cell is to be expanded, and the supernatant from the culture of each clone is to be assessed for its ability to bind immunospecifically with authentic PB39 antigen. Clones identified as successfully secreting binding antibodies are to be retained and stored. Monoclonal anti-PB39 antibodies from such clones are obtained by culturing these clones.

Example 12

ELISA Assay for PB39 in Prostate Tissue

Prostate tissue is to be obtained from a subject. If desired, the tissue is to be microdissected to extract cancerous and normal epithelial cells. The tissue sample is to be homogenized. The wells of a microtiter plate are to be contacted with polyclonal anti-PB39 from Example 10 to adsorb the antibody, and remaining sites blocked with casein. Portions of the homogenate are then to be added to the wells of the plate. Aliquots of authentic PB39 antigen at known concentrations are to be added to additional wells to serve as standards for quantitation of the amount of antigen. The wells are then to be treated with either a monoclonal anti-PB39 antibody from Example 10, or with a further aliquot of the polyclonal antibody. This second antibody will previously have been conjugated with horse radish peroxidase. The wells are then treated with the chromogenic substrate o-phenylenediamine dihydrochloride, and the resulting color is to be determined on a microtiter plate spectrophotometric detector. The absorbance values so obtained are calibrated against the PB39 standard for quantitating the amount of antigen present in the samples. Of course, other visualizing or detecting systems known in the art can be used if desired.

We claim:

1. A purified nucleic acid molecule selected from the group consisting of:
   (A) a nucleic acid molecule that comprises the sequence of SEQ ID NO:1; and
   (B) the complete full-length complement of said nucleic acid molecule (A).

2. The nucleic acid described in claim 1, wherein the nucleic acid is an RNA.

3. The nucleic acid described in claim 1, wherein the nucleic acid is a cDNA.

4. A purified nucleic acid molecule selected from the group consisting of:
   (A) the nucleic acid molecule that comprises the sequence of nucleotide 77 through nucleotide 1753 of SEQ ID NO:1; and
   (B) the complete full-length complement of said nucleic acid molecule (A).

5. The nucleic acid described in claim 4, wherein the nucleic acid is an RNA.

6. The nucleic acid described in claim 4, wherein the nucleic acid is a cDNA.

7. A purified nucleic acid selected from the group consisting of:
   (A) a nucleic acid molecule that consists of a sequence selected from the group consisting of SEQ ID NO:7, SEQ ID NO:8, and SEQ ID NO:10; and
   (B) the complete full-length complement of said nucleic acid molecule (A).

8. A method of detecting prostate cancer in a subject, said method comprising the steps:
   (A) obtaining a sample of a tissue from a primary prostate cancer or blood, urine or seminal fluid from said subject, and
   (B) determining whether said sample contains an increased level compared to a normal control of a nucleic acid molecule selected from the group consisting of:
      (1) the nucleic acid molecule that comprises the sequence of SEQ ID NO:1; and
      (2) the complete full-length complement of said nucleic acid molecule (1);
   wherein detection of said increased level of said nucleic acid molecule is indicative of the presence of prostate cancer in said subject.

9. The method described in claim 8, wherein the sample is blood, urine or seminal fluid.

10. The method described in claim 8, wherein the determining step comprises amplifying the nucleic acid and detecting the amplified nucleic acid.

11. A method of detecting prostate cancer in a subject, said method comprising the steps:
    (A) obtaining a sample of a tissue from a primary prostate cancer or blood, urine or seminal fluid from said subject, and
    (B) determining whether said sample contains an increased level compared to a normal control of a nucleic acid molecule selected from the group consisting of:
       (1) the nucleic acid molecule that comprises the sequence of nucleotide 77 through nucleotide 1753 of SEQ ID NO:1; and
       (2) the complete full-length complement of said nucleic acid molecule (1);
    wherein detection of said increased level of said nucleic acid molecule in indicative of the presence of prostate cancer in said subject.

12. The method described in claim 11, wherein the sample is blood, urine or seminal fluid.

13. The method described in claim 11, wherein the determining step comprises amplifying the nucleic acid and detecting the amplified nucleic acid.

* * * * *

SEQUENCE LISTING

```
<160> NUMBER OF SEQ ID NOS: 17

<210> SEQ ID NO 1
<211> LENGTH: 2326
<212> TYPE: DNA
<213> ORGANISM: Homo sapiens
<220> FEATURE:
<221> NAME/KEY: CDS
<222> LOCATION: (77)...(1753)

<400> SEQUENCE: 1
ccggggctgg agggggggcaa gcgggttccg aggtgcaaag cctggtgccc cgagccctgc         60
ggagctcggg gccagc atg gcc ccc acg ctg caa cag gcg tac cgg agg cgc        112
              Met Ala Pro Thr Leu Gln Gln Ala Tyr Arg Arg Arg
                1               5                  10 tgg tgg atg gcc tgc acg gct gtg ctg gag aac ctc ttc ttc tct gct          160
Trp Trp Met Ala Cys Thr Ala Val Leu Glu Asn Leu Phe Phe Ser Ala
        15                  20                  25 gta ctc ctg ggc tgg ggc tcc ctg ttg atc att ctg aag aac gag ggc          208
Val Leu Leu Gly Trp Gly Ser Leu Leu Ile Ile Leu Lys Asn Glu Gly
    30                  35                  40 ttc tat tcc agc acg tgc cca gct gag agc agc acc aac acc acc cag          256
Phe Tyr Ser Ser Thr Cys Pro Ala Glu Ser Ser Thr Asn Thr Thr Gln
 45                  50                  55                  60 gat gag cag cgc agg tgg cca ggc tgt gac cag cag gac gag atg ctc          304
Asp Glu Gln Arg Arg Trp Pro Gly Cys Asp Gln Gln Asp Glu Met Leu
                65                  70                  75 aac ctg ggc ttc acc att ggt tcc ttc gtg ctc agc gcc acc acc ctg          352
Asn Leu Gly Phe Thr Ile Gly Ser Phe Val Leu Ser Ala Thr Thr Leu
            80                  85                  90 cca ctg ggg atc ctc atg gac cgc ttt ggc ccc cga ccc gtg cgg ctg          400
```

-continued

```
                    Pro Leu Gly Ile Leu Met Asp Arg Phe Gly Pro Arg Pro Val Arg Leu
                                 95                 100                 105 gtt ggc agt gcc tgc ttc act gcg tcc tgc acc ctc atg gcc ctg gcc                    448
Val Gly Ser Ala Cys Phe Thr Ala Ser Cys Thr Leu Met Ala Leu Ala
    110                 115                 120 tcc cgg gac gtg gaa gct ctg tct ccg ttg ata ttc ctg gcg ctg tcc                    496
Ser Arg Asp Val Glu Ala Leu Ser Pro Leu Ile Phe Leu Ala Leu Ser
125                 130                 135                 140 ctg aat ggc ttt ggt ggc atc tgc cta acg ttc act tca ctc acg ctg                    544
Leu Asn Gly Phe Gly Gly Ile Cys Leu Thr Phe Thr Ser Leu Thr Leu
            145                 150                 155 ccc aac atg ttt ggg aac ctg cgc tcc acg tta atg gcc ctc atg att                    592
Pro Asn Met Phe Gly Asn Leu Arg Ser Thr Leu Met Ala Leu Met Ile
        160                 165                 170 ggc tct tac gcc tct tct gcc att acg ttc cca gga atc aag ctg atc                    640
Gly Ser Tyr Ala Ser Ser Ala Ile Thr Phe Pro Gly Ile Lys Leu Ile
    175                 180                 185 tac gat gcc ggt gtg gcc ttc gtg gtc atc atg ttc acc tgg tct ggc                    688
Tyr Asp Ala Gly Val Ala Phe Val Val Ile Met Phe Thr Trp Ser Gly
    190                 195                 200 ctg gcc tgc ctt atc ttt ctg aac tgc acc ctc aac tgg ccc atc gaa                    736
Leu Ala Cys Leu Ile Phe Leu Asn Cys Thr Leu Asn Trp Pro Ile Glu
205                 210                 215                 220 gcc ttt cct gcc cct gag gaa gtc aat tac acg aag aag atc aag ctg                    784
Ala Phe Pro Ala Pro Glu Glu Val Asn Tyr Thr Lys Lys Ile Lys Leu
            225                 230                 235 agt ggg ctg gcc ctg gac cac aag gtg aca ggt gac ctc ttc tac acc                    832
Ser Gly Leu Ala Leu Asp His Lys Val Thr Gly Asp Leu Phe Tyr Thr
        240                 245                 250 cat gtg acc acc atg ggc cag agg ctc agc cag aag gcc ccc agc ctg                    880
His Val Thr Thr Met Gly Gln Arg Leu Ser Gln Lys Ala Pro Ser Leu
    255                 260                 265 gag gac ggt tcg gat gcc ttc atg tca ccc cag gat gtt cgg ggc acc                    928
Glu Asp Gly Ser Asp Ala Phe Met Ser Pro Gln Asp Val Arg Gly Thr
    270                 275                 280 tca gaa aac ctt cct gag agg tct gtc ccc tta cgc aag agc ctc tgc                    976
Ser Glu Asn Leu Pro Glu Arg Ser Val Pro Leu Arg Lys Ser Leu Cys
285                 290                 295                 300 tcc ccc act ttc ctg tgg agc ctc ctc acc atg ggc atg acc cag ctg                   1024
Ser Pro Thr Phe Leu Trp Ser Leu Leu Thr Met Gly Met Thr Gln Leu
            305                 310                 315 cgg atc atc ttc tac atg gct gct gtg aac aag atg ctg gag tac ctt                   1072
Arg Ile Ile Phe Tyr Met Ala Ala Val Asn Lys Met Leu Glu Tyr Leu
        320                 325                 330 gtg act ggt ggc cag gag cat gag aca aat gaa cag caa caa aag gtg                   1120
Val Thr Gly Gly Gln Glu His Glu Thr Asn Glu Gln Gln Gln Lys Val
    335                 340                 345 gca gag aca gtt ggg ttc tac tcc tcc gtc ttc ggg gcc atg cag ctg                   1168
Ala Glu Thr Val Gly Phe Tyr Ser Ser Val Phe Gly Ala Met Gln Leu
    350                 355                 360 ttg tgc ctt ctc acc tgc ccc ctc att ggc tac atc atg gac tgg cgg                   1216
Leu Cys Leu Leu Thr Cys Pro Leu Ile Gly Tyr Ile Met Asp Trp Arg
365                 370                 375                 380 atc aag gac tgc gtg gac gcc cca act cag ggc act gtc ctc gga gat                   1264
Ile Lys Asp Cys Val Asp Ala Pro Thr Gln Gly Thr Val Leu Gly Asp
            385                 390                 395 gcc agg gac ggg gtt gct acc aaa tcc atc aga cca cgc tac tgc aag                   1312
Ala Arg Asp Gly Val Ala Thr Lys Ser Ile Arg Pro Arg Tyr Cys Lys
        400                 405                 410
```

| | | | | | | | | | | | | | | | |
|---|---|---|---|---|---|---|---|---|---|---|---|---|---|---|---|
| atc | caa | aag | ctc | acc | aat | gcc | atc | agt | gcc | ttc | acc | ctg | acc | aac | ctg | 1360 |
| Ile | Gln | Lys | Leu | Thr | Asn | Ala | Ile | Ser | Ala | Phe | Thr | Leu | Thr | Asn | Leu |
| | | 415 | | | | 420 | | | | 425 | | | | ctg ctt gtg ggt ttt ggc atc acc tgt ctc atc aac aac tta cac ctc 1408
Leu Leu Val Gly Phe Gly Ile Thr Cys Leu Ile Asn Asn Leu His Leu
    430                 435                 440 cag ttt gtg acc ttt gtc ctg cac acc att gtt cga ggt ttc ttc cac 1456
Gln Phe Val Thr Phe Val Leu His Thr Ile Val Arg Gly Phe Phe His
445                 450                 455                 460 tca gcc tgt ggg agt ctc tat gct gca gtg ttc cca tcc aac cac ttt 1504
Ser Ala Cys Gly Ser Leu Tyr Ala Ala Val Phe Pro Ser Asn His Phe
                465                 470                 475 ggg acg ctg aca ggc ctg cag tcc ctc atc agt gct gtg ttc gcc ttg 1552
Gly Thr Leu Thr Gly Leu Gln Ser Leu Ile Ser Ala Val Phe Ala Leu
            480                 485                 490 ctt cag cag cca ctt ttc atg gcg atg gtg gga ccc ctg aaa gga gag 1600
Leu Gln Gln Pro Leu Phe Met Ala Met Val Gly Pro Leu Lys Gly Glu
        495                 500                 505 ccc ttc tgg gtg aat ctg ggc ctc ctg cta ttc tca ctc ctg gga ttc 1648
Pro Phe Trp Val Asn Leu Gly Leu Leu Leu Phe Ser Leu Leu Gly Phe
    510                 515                 520 ctg ttg cct tcc tac ctc ttc tat tac cgt gcc cgg ctc cag cag gag 1696
Leu Leu Pro Ser Tyr Leu Phe Tyr Tyr Arg Ala Arg Leu Gln Gln Glu
525                 530                 535                 540 tac gcc gcc aat ggg atg ggc cca ctg aag gtg ctt agc ggc tct gag 1744
Tyr Ala Ala Asn Gly Met Gly Pro Leu Lys Val Leu Ser Gly Ser Glu
                545                 550                 555 gtg acc gca tagacttctc agaccaaggg acctggatga caggcaatca 1793
Val Thr Ala aggcctgagc aaccaaaagg agtgcccat atggctttc tacctgtaac atgcacatag 1853 agccatggcc gtagatttat aaataccaag agaagttcta tttttgtaaa gactgcaaaa 1913 aggaggaaaa aaaaccttca aaaacgcccc ctaagtcaac gctccattga ctgaagacag 1973 tccctatcct agagggttg agctttcttc ctccttgggt tggaggagac cagggtgcct 2033 cttatctcct tctagcggtc tgcctcctgg tacctcttgg ggggatcggc aaacaggcta 2093 cccctgaggt cccatgtgcc atgagtgtgc acaacatgca atgtgtctgt gtatgtgtga 2153 atgtgagaaa aacacagccc tcctttcaga aggaaagggg cctgaggtgc cagctgtgtc 2213 ctgggttagg ggttgggggt cggccccttc cagggccagg aaggcaggtt ccctctctgg 2273 tgctgctgct tgcaagtctt agaggaaata aaagggaag tgagaaaaaa aaa 2326

<210> SEQ ID NO 2
<211> LENGTH: 559
<212> TYPE: PRT
<213> ORGANISM: Homo sapiens

<400> SEQUENCE: 2

Met Ala Pro Thr Leu Gln Gln Ala Tyr Arg Arg Arg Trp Trp Met Ala
1               5                   10                  15

Cys Thr Ala Val Leu Glu Asn Leu Phe Phe Ser Ala Val Leu Leu Gly
            20                  25                  30

Trp Gly Ser Leu Leu Ile Ile Leu Lys Asn Glu Gly Phe Tyr Ser Ser
        35                  40                  45

Thr Cys Pro Ala Glu Ser Ser Thr Asn Thr Thr Gln Asp Glu Gln Arg
    50                  55                  60

Arg Trp Pro Gly Cys Asp Gln Gln Asp Glu Met Leu Asn Leu Gly Phe
65                  70                  75                  80

-continued

```
Thr Ile Gly Ser Phe Val Leu Ser Ala Thr Thr Leu Pro Leu Gly Ile
                85                  90                  95
Leu Met Asp Arg Phe Gly Pro Arg Pro Val Arg Leu Val Gly Ser Ala
            100                 105                 110
Cys Phe Thr Ala Ser Cys Thr Leu Met Ala Leu Ala Ser Arg Asp Val
            115                 120                 125
Glu Ala Leu Ser Pro Leu Ile Phe Leu Ala Leu Ser Leu Asn Gly Phe
            130                 135                 140
Gly Gly Ile Cys Leu Thr Phe Thr Ser Leu Thr Leu Pro Asn Met Phe
145                 150                 155                 160
Gly Asn Leu Arg Ser Thr Leu Met Ala Leu Met Ile Gly Ser Tyr Ala
                165                 170                 175
Ser Ser Ala Ile Thr Phe Pro Gly Ile Lys Leu Ile Tyr Asp Ala Gly
                180                 185                 190
Val Ala Phe Val Val Ile Met Phe Thr Trp Ser Gly Leu Ala Cys Leu
            195                 200                 205
Ile Phe Leu Asn Cys Thr Leu Asn Trp Pro Ile Glu Ala Phe Pro Ala
210                 215                 220
Pro Glu Glu Val Asn Tyr Thr Lys Lys Ile Lys Leu Ser Gly Leu Ala
225                 230                 235                 240
Leu Asp His Lys Val Thr Gly Asp Leu Phe Tyr Thr His Val Thr Thr
                245                 250                 255
Met Gly Gln Arg Leu Ser Gln Lys Ala Pro Ser Leu Glu Asp Gly Ser
                260                 265                 270
Asp Ala Phe Met Ser Pro Gln Asp Val Arg Gly Thr Ser Glu Asn Leu
            275                 280                 285
Pro Glu Arg Ser Val Pro Leu Arg Lys Ser Leu Cys Ser Pro Thr Phe
            290                 295                 300
Leu Trp Ser Leu Leu Thr Met Gly Met Thr Gln Leu Arg Ile Ile Phe
305                 310                 315                 320
Tyr Met Ala Ala Val Asn Lys Met Leu Glu Tyr Leu Val Thr Gly Gly
                325                 330                 335
Gln Glu His Glu Thr Asn Glu Gln Gln Lys Val Ala Glu Thr Val
            340                 345                 350
Gly Phe Tyr Ser Ser Val Phe Gly Ala Met Gln Leu Leu Cys Leu Leu
            355                 360                 365
Thr Cys Pro Leu Ile Gly Tyr Ile Met Asp Trp Arg Ile Lys Asp Cys
370                 375                 380
Val Asp Ala Pro Thr Gln Gly Thr Val Leu Gly Asp Ala Arg Asp Gly
385                 390                 395                 400
Val Ala Thr Lys Ser Ile Arg Pro Arg Tyr Cys Lys Ile Gln Lys Leu
                405                 410                 415
Thr Asn Ala Ile Ser Ala Phe Thr Leu Thr Asn Leu Leu Leu Val Gly
                420                 425                 430
Phe Gly Ile Thr Cys Leu Ile Asn Asn Leu His Leu Gln Phe Val Thr
            435                 440                 445
Phe Val Leu His Thr Ile Val Arg Gly Phe Phe His Ser Ala Cys Gly
            450                 455                 460
Ser Leu Tyr Ala Ala Val Phe Pro Ser Asn His Phe Gly Thr Leu Thr
465                 470                 475                 480
Gly Leu Gln Ser Leu Ile Ser Ala Val Phe Ala Leu Leu Gln Gln Pro
                485                 490                 495
```

```
Leu Phe Met Ala Met Val Gly Pro Leu Lys Gly Glu Pro Phe Trp Val
            500                 505                 510

Asn Leu Gly Leu Leu Leu Phe Ser Leu Leu Gly Phe Leu Leu Pro Ser
        515                 520                 525

Tyr Leu Phe Tyr Tyr Arg Ala Arg Leu Gln Gln Glu Tyr Ala Ala Asn
        530                 535                 540

Gly Met Gly Pro Leu Lys Val Leu Ser Gly Ser Glu Val Thr Ala
545                 550                 555
```

<210> SEQ ID NO 3
<211> LENGTH: 3442
<212> TYPE: DNA
<213> ORGANISM: Homo sapiens
<220> FEATURE:
<221> NAME/KEY: CDS
<222> LOCATION: (1760)...(3439)

<400> SEQUENCE: 3

| | | | | | |
|---|---|---|---|---|---|
| ccggggctgg | agggggggcaa | gcgggttccg | aggtgcaaag | cctggtgccc | cgagccctgc | 60 |
| ggagctcggg | gccagcatgg | cccccacgct | gcaacaggcg | taccggaggc | gctggtggat | 120 |
| ggcctgcacg | gctgtgctgg | agaacctctt | cttctctgct | gtactcctgg | gctggggctc | 180 |
| cctgttgatc | attctgaaga | cgagggcttc | ctattccagc | acgtgcccag | ctgagagcag | 240 |
| caccaacacc | acccaggatg | agcagcgcag | gtggccaggc | tgtgaccagc | aggacgagat | 300 |
| gctcaacctg | gccttcacca | ttggttcctt | cgtgctcagc | gccaccaccc | tgccactggg | 360 |
| gatcctcatg | gaccgctttg | ccccccgacc | cgtgcgctg | gttggcagtg | cctgcttcac | 420 |
| tgcgtcctgc | accctcatgg | ccctggcctc | ccgggacgtg | gaagctctgt | ctccgttgat | 480 |
| attcctggcg | ctgtccctga | atggctttgg | tggcatctgc | ctaacgttca | cttcactcac | 540 |
| gctgcccaac | atgtttggga | acctgcgctc | cacgttaatg | ccctcatga | ttggctctta | 600 |
| cgcctcttct | gccattacgt | tcccaggaat | caagctgatc | tacgatgccg | gtgtggcctt | 660 |
| cgtggtcatc | atgttcacct | ggtctggcct | ggcctgcctt | atctttctga | actgcaccct | 720 |
| caactggccc | atcgaagcct | ttcctgcccc | tgaggaagtc | aattacacga | agaagatcaa | 780 |
| gctgagtggg | ctggccctgg | accacaaggt | gacaggtgac | ctcttctaca | cccatgtgac | 840 |
| caccatgggc | cagaggctca | gccagaaggc | ccccagcctg | gaggacggtt | cggatgcctt | 900 |
| catgtcaccc | caggatgttc | ggggcacctc | agaaaacctt | cctgagaggt | ctgtcccctt | 960 |
| acgcaagagc | ctctgctccc | ccactttcct | gtggagcctc | ctcaccatgg | gcatgaccca | 1020 |
| gctgcggatc | atcttctaca | tggctgctgt | gaacaagatg | ctggagtacc | ttgtgactgg | 1080 |
| tggccaggag | catgagacaa | atgaacagca | acaaaaggtg | gcagagacag | ttgggttcta | 1140 |
| ctcctccgtc | ttcggggcca | tgcagctgtt | gtgccttctc | acctgccccc | tcattggcta | 1200 |
| catcatggac | tggcggatca | aggactgcgt | ggacgcccca | actcagggca | ctgtcctcgg | 1260 |
| agatgccagg | gacggggttg | ctaccaaatc | catcagacca | cgctactgca | agatccaaaa | 1320 |
| gctcaccaat | gccatcagtg | ccttcaccct | gaccaacctg | ctgcttgtgg | gtttttggcat | 1380 |
| cacctgtctc | atcaacaact | acacctccca | gtttgtgacc | tttgtcctgc | acaccattgt | 1440 |
| tcgaggtttc | ttccactcag | cctgtgggag | tctctatgct | gcagtgttcc | catccaacca | 1500 |
| ctttgggacg | ctgacaggcc | tgcagtccct | catcagtgct | gtgttcgcct | tgcttcagca | 1560 |
| gccactttc | atggcgatgg | tgggacccct | gaaaggagag | cccttctggg | tgagagcgag | 1620 |
| ggttggtgtg | gggggagcag | gagccactct | cctgggggca | ggggtagggc | cttgtatgtg | 1680 |

```
                                                          -continued gtgccatccc tcactcatct cagccagagg cacctcagag gtctctaatc tgcaggtttc       1740
caagttgtct gccttttag atg gcc ccc acg ctg caa cag gcg tac cgg agg        1792
                     Met Ala Pro Thr Leu Gln Gln Ala Tyr Arg Arg
                      1               5                       10 cgc tgg tgg atg gcc tgc acg gct gtg ctg gag aac ctc ttc ttc tct         1840
Arg Trp Trp Met Ala Cys Thr Ala Val Leu Glu Asn Leu Phe Phe Ser
             15                  20                  25 gct gta ctc ctg ggc tgg ggc tcc ctg ttg atc att ctg aag aac gag         1888
Ala Val Leu Leu Gly Trp Gly Ser Leu Leu Ile Ile Leu Lys Asn Glu
             30                  35                  40 ggc ttc tat tcc agc acg tgc cca gct gag agc agc acc aac acc acc         1936
Gly Phe Tyr Ser Ser Thr Cys Pro Ala Glu Ser Ser Thr Asn Thr Thr
         45                  50                  55 cag gat gag cag cgc agg tgg cca ggc tgt gac cag cag gac gag atg         1984
Gln Asp Glu Gln Arg Arg Trp Pro Gly Cys Asp Gln Gln Asp Glu Met
 60                  65                  70                  75 ctc aac ctg ggc ttc acc att ggt tcc ttc gtg ctc agc gcc acc acc         2032
Leu Asn Leu Gly Phe Thr Ile Gly Ser Phe Val Leu Ser Ala Thr Thr
                 80                  85                  90 ctg cca ctg ggg atc ctc atg gac cgc ttt ggc ccc cga ccc gtg cgg         2080
Leu Pro Leu Gly Ile Leu Met Asp Arg Phe Gly Pro Arg Pro Val Arg
                 95                 100                 105 ctg gtt ggc agt gcc tgc ttc act gcg tcc tgc acc ctc atg gcc ctg         2128
Leu Val Gly Ser Ala Cys Phe Thr Ala Ser Cys Thr Leu Met Ala Leu
            110                 115                 120 gcc tcc cgg gac gtg gaa gct ctg tct ccg ttg ata ttc ctg gcg ctg         2176
Ala Ser Arg Asp Val Glu Ala Leu Ser Pro Leu Ile Phe Leu Ala Leu
            125                 130                 135 tcc ctg aat ggc ttt ggt ggc atc tgc cta acg ttc act tca ctc acg         2224
Ser Leu Asn Gly Phe Gly Gly Ile Cys Leu Thr Phe Thr Ser Leu Thr
140                 145                 150                 155 ctg ccc aac atg ttt ggg aac ctg cgc tcc acg tta atg gcc ctc atg         2272
Leu Pro Asn Met Phe Gly Asn Leu Arg Ser Thr Leu Met Ala Leu Met
                160                 165                 170 att ggc tct tac gcc tct tct gcc att acg ttc cca gga atc aag ctg         2320
Ile Gly Ser Tyr Ala Ser Ser Ala Ile Thr Phe Pro Gly Ile Lys Leu
            175                 180                 185 atc tac gat gcc ggt gtg gcc ttc gtg gtc atc atg ttc acc tgg tct         2368
Ile Tyr Asp Ala Gly Val Ala Phe Val Val Ile Met Phe Thr Trp Ser
            190                 195                 200 ggc ctg gcc tgc ctt atc ttt ctg aac tgc acc ctc aac tgg ccc atc         2416
Gly Leu Ala Cys Leu Ile Phe Leu Asn Cys Thr Leu Asn Trp Pro Ile
            205                 210                 215 gaa gcc ttt cct gcc cct gag gaa gtc aat tac acg aag aag atc aag         2464
Glu Ala Phe Pro Ala Pro Glu Glu Val Asn Tyr Thr Lys Lys Ile Lys
220                 225                 230                 235 ctg agt ggg ctg gcc ctg gac cac aag gtg aca ggt gac ctc ttc tac         2512
Leu Ser Gly Leu Ala Leu Asp His Lys Val Thr Gly Asp Leu Phe Tyr
                240                 245                 250 acc cat gtg acc acc atg ggc cag agg ctc agc cag aag gcc ccc agc         2560
Thr His Val Thr Thr Met Gly Gln Arg Leu Ser Gln Lys Ala Pro Ser
            255                 260                 265 ctg gag gac ggt tcg gat gcc ttc atg tca ccc cag gat gtt cgg ggc         2608
Leu Glu Asp Gly Ser Asp Ala Phe Met Ser Pro Gln Asp Val Arg Gly
            270                 275                 280 acc tca gaa aac ctt cct gag agg tct gtc ccc tta cgc aag agc ctc         2656
Thr Ser Glu Asn Leu Pro Glu Arg Ser Val Pro Leu Arg Lys Ser Leu
            285                 290                 295 tgc tcc ccc act ttc ctg tgg agc ctc ctc acc atg ggc atg acc cag         2704
```

-continued

```
Cys Ser Pro Thr Phe Leu Trp Ser Leu Leu Thr Met Gly Met Thr Gln
300                 305                 310                 315 ctg cgg atc atc ttc tac atg gct gct gtg aac aag atg ctg gag tac      2752
Leu Arg Ile Ile Phe Tyr Met Ala Ala Val Asn Lys Met Leu Glu Tyr
            320                 325                 330 ctt gtg act ggt ggc cag gag cat gag aca aat gaa cag caa caa aag      2800
Leu Val Thr Gly Gly Gln Glu His Glu Thr Asn Glu Gln Gln Gln Lys
        335                 340                 345 gtg gca gag aca gtt ggg ttc tac tcc tcc gtc ttc ggg gcc atg cag      2848
Val Ala Glu Thr Val Gly Phe Tyr Ser Ser Val Phe Gly Ala Met Gln
    350                 355                 360 ctg ttg tgc ctt ctc acc tgc ccc ctc att ggc tac atc atg gac tgg      2896
Leu Leu Cys Leu Leu Thr Cys Pro Leu Ile Gly Tyr Ile Met Asp Trp
365                 370                 375 cgg atc aag gac tgc gtg gac gcc cca act cag ggc act gtc ctc gga      2944
Arg Ile Lys Asp Cys Val Asp Ala Pro Thr Gln Gly Thr Val Leu Gly
380                 385                 390                 395 gat gcc agg gac ggg gtt gct acc aaa tcc atc aga cca cgc tac tgc      2992
Asp Ala Arg Asp Gly Val Ala Thr Lys Ser Ile Arg Pro Arg Tyr Cys
            400                 405                 410 aag atc caa aag ctc acc aat gcc atc agt gcc ttc acc ctg acc aac      3040
Lys Ile Gln Lys Leu Thr Asn Ala Ile Ser Ala Phe Thr Leu Thr Asn
        415                 420                 425 ctg ctg ctt gtg ggt ttt ggc atc acc tgt ctc atc aac aac tta cac      3088
Leu Leu Leu Val Gly Phe Gly Ile Thr Cys Leu Ile Asn Asn Leu His
    430                 435                 440 ctc cag ttt gtg acc ttt gtc ctg cac acc att gtt cga ggt ttc ttc      3136
Leu Gln Phe Val Thr Phe Val Leu His Thr Ile Val Arg Gly Phe Phe
445                 450                 455 cac tca gcc tgt ggg agt ctc tat gct gca gtg ttc cca tcc aac cac      3184
His Ser Ala Cys Gly Ser Leu Tyr Ala Ala Val Phe Pro Ser Asn His
460                 465                 470                 475 ttt ggg acg ctg aca ggc ctg cag tcc ctc atc agt gct gtg ttc gcc      3232
Phe Gly Thr Leu Thr Gly Leu Gln Ser Leu Ile Ser Ala Val Phe Ala
            480                 485                 490 ttg ctt cag cag cca ctt ttc atg gcg atg gtg gga ccc ctg aaa gga      3280
Leu Leu Gln Gln Pro Leu Phe Met Ala Met Val Gly Pro Leu Lys Gly
        495                 500                 505 gag ccc ttc tgg gtg aga gcg agg gtt ggt gtg ggg gga gca gga gcc      3328
Glu Pro Phe Trp Val Arg Ala Arg Val Gly Val Gly Gly Ala Gly Ala
    510                 515                 520 act ctc ctg ggg gca ggg gta ggg cct tgt atg tgg tgc cat ccc tca      3376
Thr Leu Leu Gly Ala Gly Val Gly Pro Cys Met Trp Cys His Pro Ser
525                 530                 535 ctc atc tca gcc aga ggc acc tca gag gtc tct aat ctg cag gtt tcc      3424
Leu Ile Ser Ala Arg Gly Thr Ser Glu Val Ser Asn Leu Gln Val Ser
540                 545                 550                 555 aag ttg tct gcc ttt tag                                              3442
Lys Leu Ser Ala Phe
            560

<210> SEQ ID NO 4
<211> LENGTH: 560
<212> TYPE: PRT
<213> ORGANISM: Homo sapiens

<400> SEQUENCE: 4

Met Ala Pro Thr Leu Gln Gln Ala Tyr Arg Arg Trp Trp Met Ala
1               5                   10                  15

Cys Thr Ala Val Leu Glu Asn Leu Phe Phe Ser Ala Val Leu Leu Gly
```

-continued

```
                    20                  25                  30
Trp Gly Ser Leu Leu Ile Ile Leu Lys Asn Glu Gly Phe Tyr Ser Ser
                35                  40                  45
Thr Cys Pro Ala Glu Ser Ser Thr Asn Thr Thr Gln Asp Glu Gln Arg
 50                  55                  60
Arg Trp Pro Gly Cys Asp Gln Gln Asp Glu Met Leu Asn Leu Gly Phe
 65                  70                  75                  80
Thr Ile Gly Ser Phe Val Leu Ser Ala Thr Thr Leu Pro Leu Gly Ile
                85                  90                  95
Leu Met Asp Arg Phe Gly Pro Arg Pro Val Arg Leu Val Gly Ser Ala
                100                 105                 110
Cys Phe Thr Ala Ser Cys Thr Leu Met Ala Leu Ala Ser Arg Asp Val
                115                 120                 125
Glu Ala Leu Ser Pro Leu Ile Phe Leu Ala Leu Ser Leu Asn Gly Phe
                130                 135                 140
Gly Gly Ile Cys Leu Thr Phe Thr Ser Leu Thr Leu Pro Asn Met Phe
145                 150                 155                 160
Gly Asn Leu Arg Ser Thr Leu Met Ala Leu Met Ile Gly Ser Tyr Ala
                165                 170                 175
Ser Ser Ala Ile Thr Phe Pro Gly Ile Lys Leu Ile Tyr Asp Ala Gly
                180                 185                 190
Val Ala Phe Val Val Ile Met Phe Thr Trp Ser Gly Leu Ala Cys Leu
                195                 200                 205
Ile Phe Leu Asn Cys Thr Leu Asn Trp Pro Ile Glu Ala Phe Pro Ala
                210                 215                 220
Pro Glu Glu Val Asn Tyr Thr Lys Lys Ile Lys Leu Ser Gly Leu Ala
225                 230                 235                 240
Leu Asp His Lys Val Thr Gly Asp Leu Phe Tyr Thr His Val Thr Thr
                245                 250                 255
Met Gly Gln Arg Leu Ser Gln Lys Ala Pro Ser Leu Glu Asp Gly Ser
                260                 265                 270
Asp Ala Phe Met Ser Pro Gln Asp Val Arg Gly Thr Ser Glu Asn Leu
                275                 280                 285
Pro Glu Arg Ser Val Pro Leu Arg Lys Ser Leu Cys Ser Pro Thr Phe
290                 295                 300
Leu Trp Ser Leu Leu Thr Met Gly Met Thr Gln Leu Arg Ile Ile Phe
305                 310                 315                 320
Tyr Met Ala Ala Val Asn Lys Met Leu Glu Tyr Leu Val Thr Gly Gly
                325                 330                 335
Gln Glu His Glu Thr Asn Glu Gln Gln Lys Val Ala Glu Thr Val
                340                 345                 350
Gly Phe Tyr Ser Ser Val Phe Gly Ala Met Gln Leu Leu Cys Leu Leu
                355                 360                 365
Thr Cys Pro Leu Ile Gly Tyr Ile Met Asp Trp Arg Ile Lys Asp Cys
                370                 375                 380
Val Asp Ala Pro Thr Gln Gly Thr Val Leu Gly Asp Ala Arg Asp Gly
385                 390                 395                 400
Val Ala Thr Lys Ser Ile Arg Pro Arg Tyr Cys Lys Ile Gln Lys Leu
                405                 410                 415
Thr Asn Ala Ile Ser Ala Phe Thr Leu Thr Asn Leu Leu Val Gly
                420                 425                 430
Phe Gly Ile Thr Cys Leu Ile Asn Asn Leu His Leu Gln Phe Val Thr
                435                 440                 445
```

```
Phe Val Leu His Thr Ile Val Arg Gly Phe Phe His Ser Ala Cys Gly
            450                 455                 460

Ser Leu Tyr Ala Ala Val Phe Pro Ser Asn His Phe Gly Thr Leu Thr
465                 470                 475                 480

Gly Leu Gln Ser Leu Ile Ser Ala Val Phe Ala Leu Leu Gln Gln Pro
                485                 490                 495

Leu Phe Met Ala Met Val Gly Pro Leu Lys Gly Glu Pro Phe Trp Val
                500                 505                 510

Arg Ala Arg Val Gly Val Gly Gly Ala Gly Ala Thr Leu Leu Gly Ala
                515                 520                 525

Gly Val Gly Pro Cys Met Trp Cys His Pro Ser Leu Ile Ser Ala Arg
                530                 535                 540

Gly Thr Ser Glu Val Ser Asn Leu Gln Val Ser Lys Leu Ser Ala Phe
545                 550                 555                 560

<210> SEQ ID NO 5
<211> LENGTH: 18
<212> TYPE: DNA
<213> ORGANISM: Artificial Sequence
<220> FEATURE:
<223> OTHER INFORMATION: Arbitrary primer A2 from Stratagene, Inc.

<400> SEQUENCE: 5
aatctagagc tccagcag                                                18

<210> SEQ ID NO 6
<211> LENGTH: 29
<212> TYPE: DNA
<213> ORGANISM: Artificial Sequence
<220> FEATURE:
<223> OTHER INFORMATION: Zinc finger-directed primer

<400> SEQUENCE: 6
gtcgtcgaat tccacacagg agaaaagcc                                    29

<210> SEQ ID NO 7
<211> LENGTH: 22
<212> TYPE: DNA
<213> ORGANISM: Homo sapiens

<400> SEQUENCE: 7
gcatgttaca ggtagaaaag cc                                           22

<210> SEQ ID NO 8
<211> LENGTH: 21
<212> TYPE: DNA
<213> ORGANISM: Homo sapiens

<400> SEQUENCE: 8
ctggcgtatc tgaagagtct g                                            21

<210> SEQ ID NO 9
<211> LENGTH: 103
<212> TYPE: DNA
<213> ORGANISM: Homo sapiens

<400> SEQUENCE: 9
acaggaatcc ccaggagtga agaataagca ggaggcccca gattcacctt tagggcaagg  60
agagagaaac agagtcaagt aggtagtcat ctgcccttaa gcc                   103
```

```
<210> SEQ ID NO 10
<211> LENGTH: 20
<212> TYPE: DNA
<213> ORGANISM: Homo sapiens

<400> SEQUENCE: 10
gaccgcatag acttctcaga                                              20

<210> SEQ ID NO 11
<211> LENGTH: 22
<212> TYPE: DNA
<213> ORGANISM: Homo sapiens

<400> SEQUENCE: 11
tctgcaaagt ggctgagatg ag                                           22

<210> SEQ ID NO 12
<211> LENGTH: 26
<212> TYPE: DNA
<213> ORGANISM: Homo sapiens

<400> SEQUENCE: 12
cctgccttat ctttctgaac tgcacc                                       26

<210> SEQ ID NO 13
<211> LENGTH: 14
<212> TYPE: PRT
<213> ORGANISM: Artificial Sequence
<220> FEATURE:
<223> OTHER INFORMATION: Epitope

<400> SEQUENCE: 13

Thr Gln Asp Glu Gln Arg Arg Trp Pro Gly Cys Asp Gln Gln
 1               5                  10

<210> SEQ ID NO 14
<211> LENGTH: 14
<212> TYPE: PRT
<213> ORGANISM: Artificial Sequence
<220> FEATURE:
<223> OTHER INFORMATION: Epitope

<400> SEQUENCE: 14

Glu Asn Leu Pro Glu Arg Ser Val Pro Leu Arg Lys Ser Leu
 1               5                  10

<210> SEQ ID NO 15
<211> LENGTH: 13
<212> TYPE: PRT
<213> ORGANISM: Artificial Sequence
<220> FEATURE:
<223> OTHER INFORMATION: Epitope

<400> SEQUENCE: 15

Arg Pro Arg Tyr Cys Lys Ile Gln Lys Leu Thr Asn Ala
 1               5                  10

<210> SEQ ID NO 16
<211> LENGTH: 13
<212> TYPE: PRT
<213> ORGANISM: Artificial Sequence
<220> FEATURE:
<223> OTHER INFORMATION: Epitope

<400> SEQUENCE: 16

Ala Asn Gly Met Gly Pro Leu Lys Val Leu Ser Gly Ser
```

```
<210> SEQ ID NO 17
<211> LENGTH: 13
<212> TYPE: PRT
<213> ORGANISM: Artificial Sequence
<220> FEATURE:
<223> OTHER INFORMATION: Epitope

<400> SEQUENCE: 17

Ala Arg Gly Thr Ser Glu Val Ser Asn Leu Gln Val Ser
 1               5                  10
```